United States Patent [19]

Tomotake et al.

[11] Patent Number: 4,994,361
[45] Date of Patent: Feb. 19, 1991

[54] SILVER HALIDE COLOR PHOTOGRAPHIC LIGHT-SENSITIVE MATERIAL

[75] Inventors: Atsushi Tomotake; Shuji Kida; Mayumi Tomotake; Fumio Ishii, all of Hino, Japan

[73] Assignee: Konica Corporation, Tokyo, Japan

[21] Appl. No.: 441,302

[22] Filed: Nov. 27, 1989

[30] Foreign Application Priority Data

Nov. 29, 1988 [JP] Japan ................... 63-302628

[51] Int. Cl.$^5$ ............................................. G03C 7/36
[52] U.S. Cl. ............................................. 430/557; 430/389
[58] Field of Search ............................ 430/557, 389

[56] References Cited

U.S. PATENT DOCUMENTS

| 4,370,410 | 1/1983 | Iijima et al. | 430/505 |
| 4,824,773 | 4/1989 | Sato et al. | 430/557 |

FOREIGN PATENT DOCUMENTS

| 267491 | 5/1988 | European Pat. Off. | 430/557 |
| 283324 | 9/1988 | European Pat. Off. | 430/557 |
| 62-204259 | 9/1987 | Japan | 430/557 |
| 62-250446 | 10/1987 | Japan | 430/557 |
| 63-123048 | 5/1988 | Japan | 430/557 |
| 63-256952 | 10/1988 | Japan | 430/557 |
| 1-158441 | 6/1989 | Japan | 430/557 |

Primary Examiner—Paul R. Michl
Assistant Examiner—Janis L. Dote
Attorney, Agent, or Firm—Jordan B. Bierman

[57] ABSTRACT

A silver halide color photographic light-sensitive material is disclosed in which a novel yellow coupler represented by the following Formula I is contained.

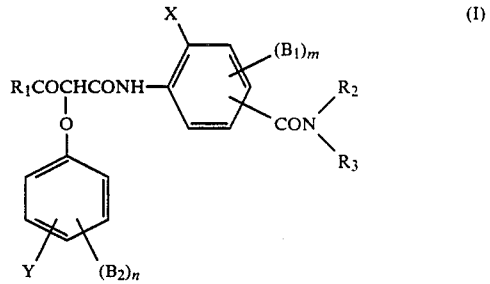

wherein $R_1$ is a substituted or unsubstituted alkyl group or a substituted or unsubstituted aryl group; $R_2$ and $R_3$ are each a hydrogen atom, a substituted or unsubstituted alkyl group or a substituted or unsubstituted aryl group or a substituted or unsubstituted heterocyclic group; X is a hydrogen atom, a halogen atom, an alkoxy group or an alkylamino group; Y, $B_1$ and $B_2$ are each a substituent; and m and n are each an integer of zero to 3.

9 Claims, No Drawings

SILVER HALIDE COLOR PHOTOGRAPHIC LIGHT-SENSITIVE MATERIAL

FIELD OF THE INVENTION

This invention relates to a silver halide color photographic light-sensitive material applied with a active-site substituted type yellow dye-forming coupler having an excellent color forming efficiency.

BACKGROUND OF THE INVENTION

In color photography, as is generally known a color image is formed in the color development process of a silver halide color photographic light-sensitive material, during which an oxidized aromatic primary amine type color developing agent couples to a coupler so as to produce a dye such as indophenol, indoaniline, azomethine, phenoxazone, quinoneimine, phenadine, and the like. In this case, a color subtraction process is generally used for color reproduction, in which the couplers forming a yellow, magenta, or cyan dye which are in the complementary color relation to the silver halide emulsions selectively sensitive to blue, green, or red, respectively. For example, as the yellow couplers forming yellow dyes, a compound having an open-chained active methylene group is generally used. As the magenta coupler forming magneta dyes, a pyrazolone, pyrazolobenzimidazole, pyrazolotriazole, or indazolone type compound is used. And, as the cyan couplers forming cyan dyes, a compound having a phenol or naphthol type hydroxyl group is used.

In general, such color couplers require reduction of 4 silver atoms to produce every one molecule of such a dye. From the viewpoint of the shortage of silver resources, a silver-saving type color coupler has been proposed. For example, as proposed in Japanese Patent Examined Publication No. 49-13576(1974), there is a well known technique using a so-called 2-equivalent type color coupler introduced a split off group into the active site thereof so that one molecule of a dye can be produced with reduction of 2 silver atoms. According to this technique, an amount of silver used may be saved by half as compared to that of a so-called 4-equivalent type coupler in conventional use. In recent years, therefore, the 2-equivalent type couplers have popularly been used.

However, there have been still demanded to further improve the characteristics of the well-known 2-equivalent type coupler, though the characteristics of the couplers are acceptable to some extent. In particular, the color forming efficiency is not satisfactory. Therefore, a highly reactive coupler has been demanded from the standpoints of making sensitivity and image quality higher and making processing time shorter, at which have strongly been aimed in recent years. In other words, the sensitivity of a light-sensitive material can be improved by enhancing the reactivity of a coupler to be reacted with the oxidized product of a developing agent. The amounts of both couplers and silver halide can be reduced as much as the amounts thereof to be used to make the sensitivity of the light-sensitive material higher by enhancing the reactivity of the couplers, provided, such high sensitization is not desired. The improvements described above will result in the im-provement of image sharpness, because the layer thickness of the light-sensitive material can be reduced so that the scattering of incident light can also be reduced. In the case of both color negative and color reversal light-sensitive materials, it is most effective in improving them to reduce the thickness of the blue-sensitive layer thereof because the blue-sensitive layer thereof is closest to the side of incident light. Therefore, it has particularly been expected to develop highly reactive yellow couplers.

On the other hand, from the aspect of development processes, benzyl alcohol has been added to the conventional type developer to enhance the color develpment efficieny of a light-sensitive material. However, benzyl alcohol has the problems of environmental pollution such as an increase of B.O.D. which stands for biological oxygen demands. In the course of a color development process, it has therefore been required to reduce an amount of benzyl alcohol used therein. On the contrary, when reducing benzyl alcohol from the developer, particularly, when making a processing time shorter, there raised a problem that a color density is seriously lowered in photograpic materials using the conventional color coupler. It has therefore been seriously demanded to develop a yellow coupler having a satisfactory color forming efficiency.

From among the conventional types of 4- and 2-equivalent yellow couplers, nothing has been found out to satisfy both of the above-mentioned problems. Apart therefrom, a 2-equivalent type yellow coupler having an aryloxy group as the split-off group thereof has attracted the general attention as a coupler satisfying both of the above-mentioned problems. For example, U.S. Pat. No. 3,644,498 discloses an aryloxygroup split-off type 2-equivalent yellow coupler having a sulfamoyl or acylamino group as the ballast group thereof; Japanese Patent Publication Open to Public Inspection (hereinafter referred to as Japanese Patent O.P.I. Publication) No. 59-174839(1984) discloses an aryloxy group split-off type 2-equivalent yellow coupler having an alkoxycarbonyl group as the ballast grou thereof: and Japanese Patent O.P.I. Publication No. 60-69653(1985) discloses an aryloxy group split-off type Z-equivalent yellow coupler having an alkyl or arylsulfamoyl group as the ballast group thereof. It has been proved that the above-given couplers can remarkably improve a color forming efficiency, particularly when introducing into the p-position of the aryloxy split-off group with such a so-called electron attractive group as a sulfonyl, sulfamoyl, carbamoyl, acyl, formyl, nitro, or cyano group. However, these couplers have had the problems that they do not fully satisfy the dissolving property to a high boiling organic solvent, due to the influence of the ballast group contained therein, and that they have had a substantially low dispersion stability in a silver halide emulsion. These facts have further proved to be more serious particularly when reducing a content of the high boiling solvent to thin the layers of a light-sensitive material so that the recent strong intention to thinned layers may be satisfied. In addition to the above, most of the couplers disclosed in the above-given patent specifications still have the problems that an amount of such couplers coated should be increased because of an unsatisfactory coupling reactivity, a low color density, and the like. A further improvement of the couplers has therefore been desired.

As the aryloxy group split-off type 2-equivalent yellow couplers further improved both of the dissolving property to a high boiling solvent and a color forming efficiency, Japanese Patent O.P.I. Publication Nos. 62-153954(1987) and 63-43144(1988) disclose the compounds having an alkyl or an arylsulfonamido group as the ballast group thereof. These couplers are the compounds with the purpose of improving an image preservability and it can still hardly be said that the color forming efficiency is satisfactory. Besides, Japanese Patent O.P.I. Publication No. 62-153955 (1987) discloses the aryloxy group split-off type 2-equivalent yellow couplers each having a peculiar arylsulfonamido group as the ballast group thereof. Even with these couplers, it cannot be said that the demands for a high dissolving property to a high boiling solvent and a high color forming efficiency can be fully satisfied and, furthermore, these couplers have another problem that the ballast group thereof is so complicated that the production costs should be increased.

U.S. Pat. No. 4,401,752, and Japanese Patent O.P.I. Publication Nos. 59-228649(1984), 62-204259(1987), and 62-250446(1987), each disclose that a color forming efficiency may further be improved particularly when introducing a substituent bonded to a hetero atom into the o-position of an aryloxy split-off group. Among these patent specifications, Japanese Patent O.P.I. Publication No. 62-204259(1987), and 62-250446(1987), each disclose the yellow couplers each having a carbamoyl group as the ballast group thereof and a substituent bonded to a hetero atom at the o-position.

However, the introduction of a substituent into a o-position of an aryloxy split-off group will result in the deteriorations in both dissolving property to a high boiling solvent and a dispersion stability in an emulsion. These couplers have therefore been unable to solve the above-mentioned conventional problems successfully.

SUMMARY OF THE INVENTION

An object of the invention to provide an inexpensive, highly sensitive or high image-quality silver halide color light-sensitive material capable of displaying both of a satisfactory dispersion-stability to a silver halide emulsion and an excellent color forming efficiency by containing a yellow coupler having a high reactivity, and obtaining a sufficient maximum color density.

The above-mentioned object of the invention can be achieved with a silver halide color light-sensitive material comprising a silver halide emulsion layer containing a coupler represented by the following Formula I.

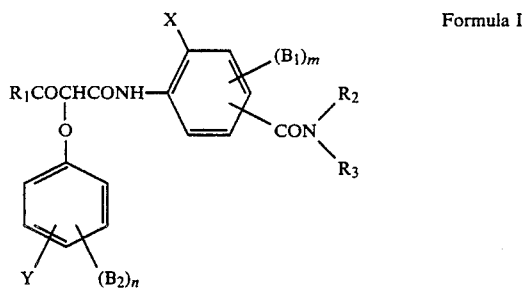

Formula I wherein $R_1$ is a substituted or unsubstituted alkyl or aryl group; $R_2$ and $R_3$ are each a hydrogen atom, a substituted or unsubstituted alkyl or aryl group, or a heterocyclic group; X is a hydrogen atom, or a halogen atom, an alkoxy or alkylamino group; Y is a substitutent; and m and n are each an interger of 0 to 3.

DETAILED DESCRIPTION OF THE INVENTION

In Formula I, the alkyl groups each represented by $R_1$ include, straight- or branched-chained or cyclic-structured alkyl groups having 1 to 30 carbon atoms such as methyl, isopropyl, t-butyl and n-dodecyl groups and, among them in particular, tertiary alkyl groups such as t-butyl groups are preferable. Further, these alkyl groups each represented by $R_1$ may have such a substituent as a halogen atom, an aryl group, an aryloxy group, a thioalkyl group, an alkylsulfonyl group, an acylamino group, a carba moyl group, an anilino group, an alkoxy group, or a hydroxy group.

In Formula I, the aryl groups each represented by $R_1$ include, for example, the aryl groups each having 6 to 30 carbon atoms, such as a phenyl or p-(t-octyl)phenyl group. The aryl groups each represented by $R_1$ may have such a substituent as a halogen atom, or an alkyl, aryl, alkoxy, aryloxy, nitro, cyano, or acylamino group.

In Formula I, the alkyl groups each represented by $R_2$ or $R_3$ include, for example, the straight- or branch-chained or cyclic-structured alkyl groups each having 1 to 30 carbon atoms, such as a t-butyl, n-hexyl, cyclohexyl, t-octyl, n-dodecyl, or n-hexadecyl group.

In Formula I, the aryl groups each represented by $R_2$ or $R_3$ include, for example, the aryl groups each having 6 to 30 carbon atoms, such as a phenyl or p-(t-octyl)phenyl group.

In Formula I, the heterocyclic groups each represented by $R_2$ or $R_3$ include, for example, a furyl, pyranyl, thienyl, pyridyl, or 2H-pyrrolyl group.

The alkyl, aryl, and heterocyclic groups represented each by $R_2$ or $R_3$ may further have such a substituent as an alkyl, aryl, hydroxy, alkoxy, aryloxy, mercapto, thioalkyl, thioaryl, amino, alkylamino, anilino, carboxyl, alkoxycarbonyl, aryloxycarbonyl, alkylcarbonylamino, arylcarbonylamino, sulfamoyl, alkylsulfamoyl, arylsulfamoyl, sulfo, alkylsulfonyl, arylsulfonyl, alkylcarbonyl, arylcarbonyl, cyano, nitro, carbamoyl, alkylcarbamoyl, arylcarbamoyl, or heterocyclic group, or a halogen atom.

In Formula I, the groups each represented by X include, for example, a hydrogen or halogen atom, or an alkoxy or alkylamino group, more preferably, a halogen atom or an alkoxy group and, more preferably, a chlorine atom or a methoxy group.

In Formula I, the substituent of the benzene ring, each represented by Y, include, for example, a halogen atom, or an alkyl, alkenyl, aryl, alkoxy, aryloxy, acyloxy, alkylamino, anilino, alkylcarbonylamino, arylcarbonylamino, alkylsulfonylamino, arylsulfonylamino, nitro, cyano, carboxyl, alkoxycarbonyl, aryloxycarbonyl, carbamoyl, alkylcarbamoyl, arylcarbamoyl, alkylcarbonyl, arylcarbonyl, mercapto, thioalkyl, thioaryl, sulfo, alkylsulfonyl, arylsulfonyl, sulfamoyl, alkylsulfamoyl, arylsulfamoyl, or heterocyclic group. Among these groups, the preferable groups include, for example, electron attractive groups such as a halogen atom, or an alkylcarbonylamino, arylcarbonylamino, alkylsulfonylamino, arylsulfonylamino, nitro, cyano, carboxyl, alkoxycarbonyl, aryloxycarbonyl, carbamoyl, alkylcarbamoyl, arylcarbamoyl, alkylcarbonyl, arylcarbonyl, sulfo, alkylsulfonyl, arylsulfonyl, sulfamoyl, alkylsulfamoyl or arylsulfamoyl group: and, more preferable groups include, for example, an alkylcarbonyl, arylcarbonyl, alkylsulfonylamino, arylsulfonylamino, nitro, cyano, carbamoyl, alkylcarbamoyl, arylcarbamoyl, alkylsulfonyl. arylsulfonyl, sulfamoyl, alkylsulfamoyl, or arylsulfamoyl group. These substituents each may further have such a substituent as a hydroxy or amino group, or a substituent synonymous with the substituents represented by Y.

In Formula I, the substituents of the benzene ring represented by $B_1$ include, for example, a halogen atom, or an alkoxy, aryloxy, acyloxy, alkylamino, anilino, or acylamino group. m is an integer of 0 to 3. When m is 2 or 3, each of $B_1$ may also represent the same substituent.

In Formula I, the substituents of the benzene ring, represented by $B_2$, include, for example, the substituents each synonymous with those represented by Y. Y and $B_2$ may also represent each the same substituent, n is an integer of 0 to 3. When n is 2 or 3, each of $B_2$ may also represent the same substituent.

In Formula I, it is preferable that each of the substituents each represented by Y or $B_2$ bond to an aryloxy split-off group at the m or p-position with respect to the oxygen atom bonding to the active site of the coupler residual group.

The couplers each represented by Formula I are also allowed to produce a dimer, oligomer, or more polymerized polymer bonding together through any divalent or more valent group of the substituents represented by $R_1$, $R_2$, $R_3$, X, Y, $B_1$, and $B_2$. In this case, it is allowed to disregard the range of the carbon atom number specified for the aforegiven substituents.

Now, the typical examples of the yellow couplers each represented by Formula I will be given below. It is however to be understood that this invention shall not be limited thereto.

| Coupler No. | R¹ | Z | Ar |
|---|---|---|---|
| (1) | $(CH_3)_3C-$ | 4-$NO_2$-phenoxy | 4-Cl-3-($CONHC_{12}H_{25}(n)$)-phenyl |
| (2) | $(CH_3)_3C-$ | 4-CN-phenoxy | 4-Cl-3-($CONHC_{12}H_{25}(n)$)-phenyl |
| (3) | $(CH_3)_3C-$ | 4-$CO_2CH_3$-phenoxy | 4-Cl-3-($CONHC_{12}H_{25}(n)$)-phenyl |
| (4) | $(CH_3)_3C-$ | 4-(4-OH-phenylsulfonyl)-phenoxy | 4-Cl-3-($CONHC_{12}H_{25}(n)$)-phenyl |
| (5) | $(CH_3)_3C-$ | 4-$NHSO_2CH_3$-phenoxy | 4-Cl-3-($CONHC_{12}H_{25}(n)$)-phenyl |

$$R^1COCHCONHAr$$
$$\phantom{R^1COCH}|$$
$$\phantom{R^1COCHCON}Z$$

-continued

| Coupler No. | R¹ | Z | Ar |
|---|---|---|---|
| (6) | $(CH_3)_3C-$ | -O-C₆H₄-SO₂N(CH₃)₂ | 4-Cl, 3-CH₃ phenyl-CONHC₁₂H₂₅(n) |
| (7) | $(CH_3)_3C-$ | -O-C₆H₄-NHCOCF₃ | 4-Cl, 3-CH₃ phenyl-CONHC₁₂H₂₅(n) |
| (8) | $(CH_3)_3C-$ | -O-C₆H₄-SO₂-C₆H₄-OCH₂Ph | 4-OCH₃, 3-CH₃ phenyl-CONHC₁₂H₂₅(n) |
| (9) | $(CH_3)_3C-$ | -O-C₆H₄-SO₂-C₆H₄-OH | 4-OCH₃, 3-CH₃ phenyl-CONHC₁₂H₂₅(n) |
| (10) | $(CH_3)_3C-$ | -O-C₆H₄-CONH-C₃H₇(i) | 4-OCH₃, 3-CH₃ phenyl-CONHC₁₂H₂₅(n) |

-continued
R¹COCHCONHAr
      |
      Z
| Coupler No. | R¹ | Z | Ar |
|---|---|---|---|
| (11) | $(CH_3)_3C-$ | 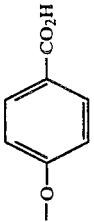 | 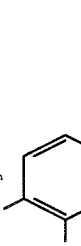 |
| (12) | $(CH_3)_3C-$ |  | 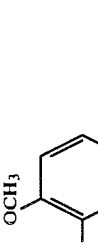 |
| (13) | $(CH_3)_3C-$ | 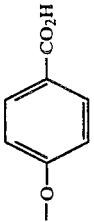 | 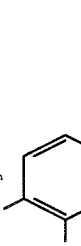 |
| (14) | $(CH_3)_3C-$ |  | 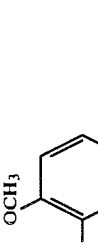 |

-continued $$R^1COCHCONHAr$$
$$|$$
$$Z$$

| Coupler No. | R¹ | Z | Ar |
|---|---|---|---|
| (15) | (CH₃)₃C— | 4-CH₃O-C₆H₄-SO₂NHC₃H₇(i) (para SO₂NHC₃H₇(i), methoxy link) | 4-Cl, 3-CH₃-C₆H₃-O-(CH₂)₄-NHCO-C₆H₃[2-C₅H₁₁(t), 4-C₅H₁₁(t)] |
| (16) | (CH₃)₃C— | 4-CH₃O-C₆H₄- with NHSO₂Ph | 4-Cl, 3-CH₃-C₆H₃-O-(CH₂)₄-NHCO-C₆H₃[2-C₅H₁₁(t), 4-C₅H₁₁(t)] |
| (17) | (CH₃)₃C— | 4-CH₃O-C₆H₄- with NO₂ | 4-Cl, 3-CH₃-C₆H₃-O-(CH₂)₄-NHCO-C₆H₃[2-C₅H₁₁(t), 4-C₅H₁₁(t)] |
| (18) | (CH₃)₃C— | 4-CH₃O-C₆H₄- with COCH₃ | 4-Cl, 3-CH₃-C₆H₃-O-(CH₂)₄-NHCO-C₆H₃[2-C₅H₁₁(t), 4-C₅H₁₁(t)] |

-continued
$$R^1COCHCONHAr$$
$$\phantom{R^1COCH}|$$
$$\phantom{R^1COCHCON}Z$$
| Coupler No. | R¹ | Z | Ar |
|---|---|---|---|
| (19) | $(CH_3)_3C-$ | 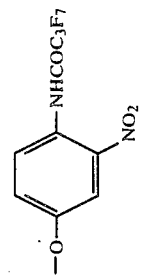 | 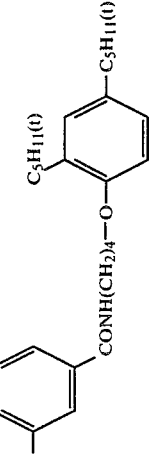 |
| (20) | $(CH_3)_3C-$ | 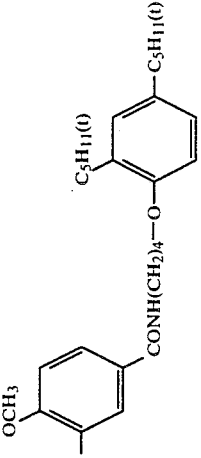 | 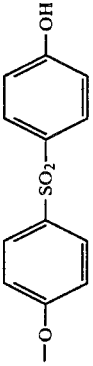 |
| (21) | $(CH_3)_3C-$ |  | 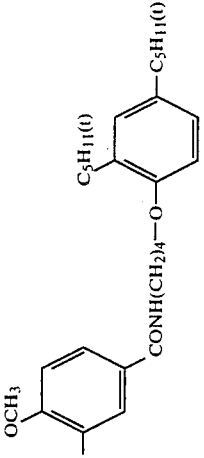 |
| (22) | $(CH_3)_3C-$ | 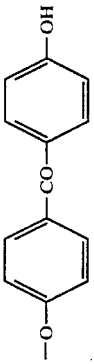 |  |

-continued $$R^1COCHCONHAr$$
$$\phantom{R^1COCHCO}|\phantom{NHAr}$$
$$\phantom{R^1COCHCONHA}Z$$

| Coupler No. | R¹ | Z | Ar |
|---|---|---|---|
| (23) | (CH₃)₃C— | 4-methoxyphenyl with NHSO₂CH₃ at ortho position | 4-methoxy-3-methylphenyl with CONH(CH₂)₄—O— linked to 2,4-di-t-pentylphenyl |
| (24) | (CH₃)₃C— | 4-methoxyphenyl with NHCOCH₃ and Cl | 4-methoxy-3-methylphenyl with CONH(CH₂)₄—O— linked to 2,4-di-t-pentylphenyl |
| (25) | (CH₃)₃C— | 3-CF₃-phenoxy | 4-methoxy-3-methylphenyl with CONH(CH₂)₄—O— linked to 2,4-di-t-pentylphenyl |
| (26) | (CH₃)₃C— | 3-OCH₃-phenoxy | 4-methoxy-3-methylphenyl with CONH(CH₂)₄—O— linked to 2,4-di-t-pentylphenyl |

-continued
$$R^1COCHCONHAr$$
$$|$$
$$Z$$
| Coupler No. | $R^1$ | Z | Ar |
|---|---|---|---|
| (27) | $(CH_3)_3C-$ | 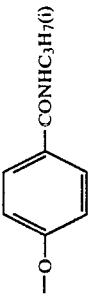 | 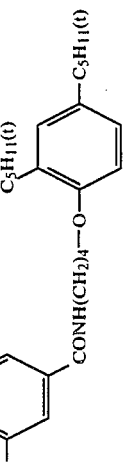 |
| (28) | $(CH_3)_3C-$ | 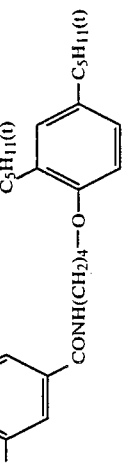 | 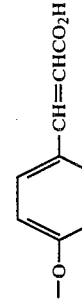 |
| (29) | $(CH_3)_3C-$ | 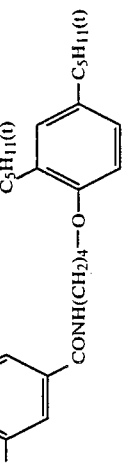 |  |
| (30) | $(CH_3)_3C-$ | 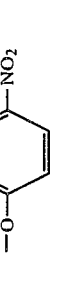 | 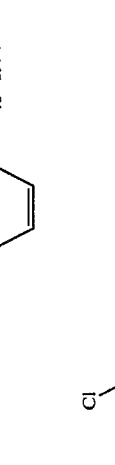 |

-continued
$$R^1COCHCONHAr$$
$$\phantom{R^1COCH}|$$
$$\phantom{R^1COCHCON}Z$$
| Coupler No. | $R^1$ | Z | Ar |
|---|---|---|---|
| (31) | $(CH_3)_3C-$ | 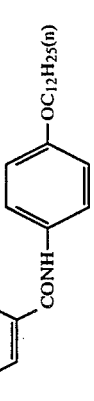 | 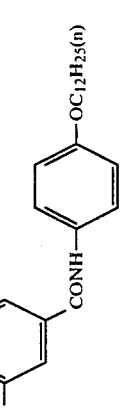 |
| (32) | $(CH_3)_3C-$ | 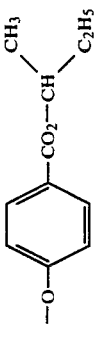 | 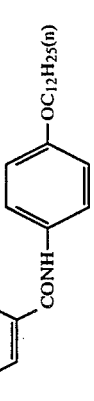 |
| (33) | $(CH_3)_3C-$ | 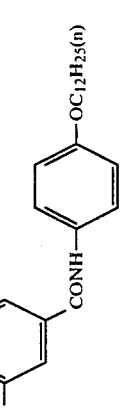 | 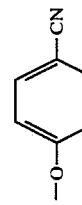 |
| (34) | $(CH_3)_3C-$ |  | 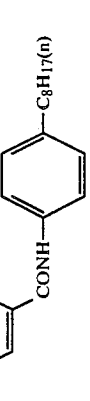 |

-continued
| Coupler No. | R¹ | Z | Ar |
|---|---|---|---|
| (35) | $(CH_3)_3C-$ | 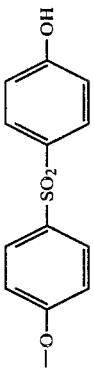 | 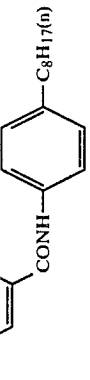 |
| (36) | $(CH_3)_3C-$ | 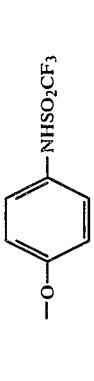 | 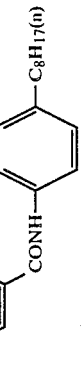 |
| (37) | $(CH_3)_3C-$ | 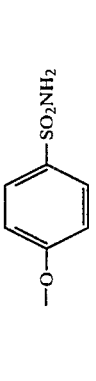 | 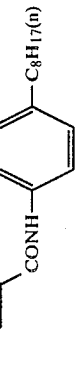 |
| (38) | $(CH_3)_3C-$ | 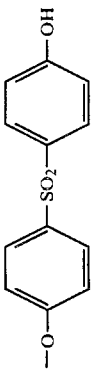 | 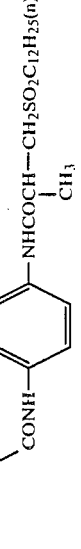 |

-continued $$R^1COCHCONHAr$$
$$\phantom{R^1COCHCON}|$$
$$\phantom{R^1COCHCONH}Z$$

| Coupler No. | $R^1$ | Z | Ar |
|---|---|---|---|
| (39) | $(CH_3)_3C-$ | 2-Cl, 4-(—O—), 1-$CO_2C_3H_7(i)$ phenyl | 3-methyl-4-methoxyphenyl-CONH-[4-(NHCOCH(CH_3)CH_2SO_2C_{12}H_{25}(n))phenyl] |
| (40) | $(CH_3)_3C-$ | 4-(—O—), 1-$NHCOCF_3$ phenyl | 3-methyl-4-methoxyphenyl-CONH-[4-(NHCOCH(CH_3)CH_2SO_2C_{12}H_{25}(n))phenyl] |
| (41) | $(CH_3)_3C-$ | 4-(—O—), 1-$NO_2$ phenyl | 3-chloro-4-methylphenyl-CONH-pyridyl-NHCOCH($C_2H_5$)O-(2-$C_5H_{11}(t)$, 4-$C_5H_{11}(t)$)phenyl |
| (42) | $(CH_3)_3C-$ | 4-(—O—), 1-$CO_2CH_3$ phenyl | 4-chloro-3-methylphenyl-O-CON(cyclohexyl)_2 |

-continued
R¹COCHCONHAr
|
Z
| Coupler No. | R¹ | Z | Ar |
|---|---|---|---|
| (43) | $(CH_3)_3C-$ | 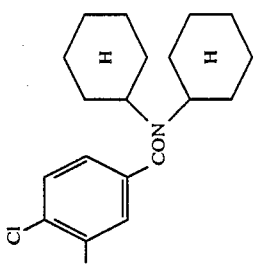 | 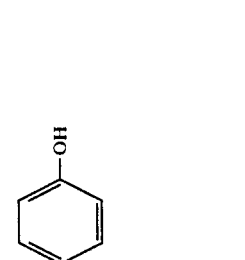 |
| (44) | $(CH_3)_3C-$ | 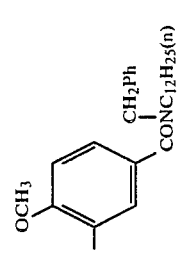 |  |
| (45) | $(CH_3)_3C-$ | 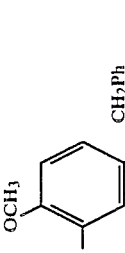 | 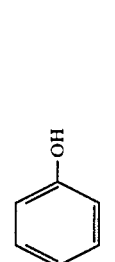 |
| (46) | $(CH_3)_3C-$ | 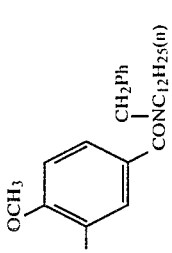 |  |

-continued
| Coupler No. | R¹ | Z | Ar |
|---|---|---|---|
| (47) | $(CH_3)_3C-$ | 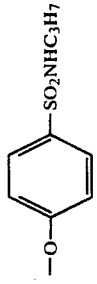 |  |
| (48) | 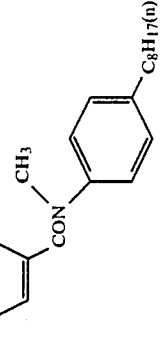 | 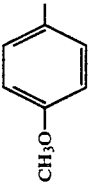 | 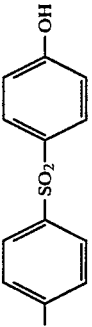 |
| (49) |  |  | 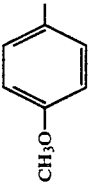 |
| (50) | 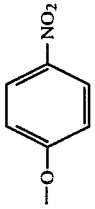 |  | 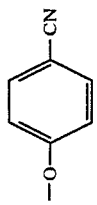 |

-continued
| Coupler No. | R¹ | Z | Ar |
|---|---|---|---|
| (51) | 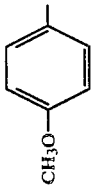 CH₃O— | 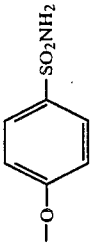 —O—⟨⟩—SO₂NH₂ | 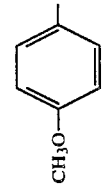 Cl—⟨⟩—CONHC₁₂H₂₅(n) |
| (52) | 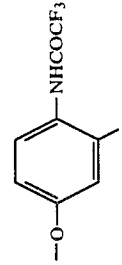 CH₃O— |  —O—⟨⟩(NHCOCF₃)(NO₂) | 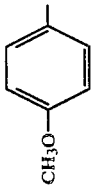 Cl—⟨⟩—CONHC₁₂H₂₅(n) |
R¹COCHCONHAr
        |
        Z $$R^1COCHCONHAr$$
$$|$$
$$Z$$

| Coupler No. | R¹ | Z | Ar |
|---|---|---|---|
| (53) | 4-CH₃O-C₆H₄- | 4-CH₃O-C₆H₄-CONH-CH₂CH₂CO₂CH₃ | 4-Cl-3-(CONHC₁₂H₂₅(n))-C₆H₃- |
| (54) | 4-CH₃O-C₆H₄- | 4-CH₃O-C₆H₄-NHSO₂CH₃ | 4-Cl-3-(CONHC₁₂H₂₅(n))-C₆H₃- |
| (55) | 4-CH₃O-C₆H₄- | 4-CH₃O-C₆H₄-O-C₆H₄-OH (via 4,4'-diphenyl ether) | 4-Cl-3-(CONHC₁₂H₂₅(n))-C₆H₃- |
| (56) | 4-CH₃O-C₆H₄- | 3-CF₃-C₆H₄-O- | 4-Cl-3-(CONHC₁₂H₂₅(n))-C₆H₃- |
| (57) | 4-CH₃O-C₆H₄- | 4-CH₃O-C₆H₄-NHCO-(CH₂)₃OCH₃ | 4-Cl-3-(CONHC₁₂H₂₅(n))-C₆H₃- |

-continued $R^1COCHCONHAr$
         |
         Z

| Coupler No. | $R^1$ | Z | Ar |
|---|---|---|---|
| (58) | 4-$CH_3O$-C$_6$H$_4$- | 4-$CH_3O$-C$_6$H$_4$-NHCO—CH$_2$CH$_2$CO$_2$H | 3-methyl-4-chlorophenyl-CONHC$_{12}$H$_{25}$(n) |
| (59) | 4-$CH_3O$-C$_6$H$_4$- | 4-$CH_3O$-C$_6$H$_4$-NO$_2$ | 4-chloro-3-methylphenyl with CONH(CH$_2$)$_4$O-(2-C$_5$H$_{11}$(t), 4-C$_5$H$_{11}$(t))phenyl |
| (60) | 4-$CH_3O$-C$_6$H$_4$- | 4-$CH_3O$-C$_6$H$_4$-SO$_2$-C$_6$H$_4$-OH | 4-chloro-3-methylphenyl with CONH(CH$_2$)$_4$O-(2-C$_5$H$_{11}$(t), 4-C$_5$H$_{11}$(t))phenyl |
| (61) | 4-$CH_3O$-C$_6$H$_4$- | 4-$CH_3O$-C$_6$H$_3$(2-Cl)(CN) | 4-chloro-3-methylphenyl with CONH(CH$_2$)$_4$O-(2-C$_5$H$_{11}$(t), 4-C$_5$H$_{11}$(t))phenyl |

-continued $$R^1COCHCONHAr$$
$$\phantom{R^1COCH}|$$
$$\phantom{R^1COCHCONHA}Z$$

| Coupler No. | R¹ | Z | Ar |
|---|---|---|---|
| (62) | 4-CH₃O-C₆H₄- | 4-(NHSO₂CH₃)-C₆H₄-O- | 4-Cl, 3-CH₃, [CONH(CH₂)₄O-(2-C₅H₁₁(t), 4-C₅H₁₁(t))C₆H₃]-C₆H₃- |
| (63) | 4-CH₃O-C₆H₄- | 4-(NHCO-CH₂CH₂CO₂H)-C₆H₄-O- | 4-Cl, 3-CH₃, [CONH(CH₂)₄O-(2-C₅H₁₁(t), 4-C₅H₁₁(t))C₆H₃]-C₆H₃- |
| (64) | 4-CH₃O-C₆H₄- | 4-(SO₂—N(CH₃)₂)-C₆H₄-O- | 4-Cl, 3-CH₃, [CONH(CH₂)₄O-(2-C₅H₁₁(t), 4-C₅H₁₁(t))C₆H₃]-C₆H₃- |
| (65) | 4-CH₃O-C₆H₄- | 4-(CONHC₃H₇)-C₆H₄-O- | 4-Cl, 3-CH₃, [CONH(CH₂)₄O-(2-C₅H₁₁(t), 4-C₅H₁₁(t))C₆H₃]-C₆H₃- |

-continued

| Coupler No. | R¹ | Z | Ar |
|---|---|---|---|
| (66) | 4-CH₃O-C₆H₄- | 3,5-dichloro-1-methoxyphenyl | 4-chloro-3-methyl-phenyl-CONH-(with CONH(CH₂)₄O-, 2-C₅H₁₁(t), 5-C₅H₁₁(t) substituents) |
| (67) | 4-CH₃O-C₆H₄- | 4-methoxy-phenyl-SO₂CH₃ | 4-chloro-3-methyl-phenyl-CONH-C₆H₄-NHSO₂C₈H₁₇(n) |
| (68) | 4-CH₃O-C₆H₄- | 4-(4-hydroxyphenoxy)-1-methoxyphenyl | 4-chloro-3-methyl-phenyl-CONH-C₆H₄-NHSO₂C₈H₁₇(n) |
| (69) | 4-CH₃O-C₆H₄- | 2-chloro-4-methoxy-phenyl-CN | 4-chloro-3-methyl-phenyl-CONH-C₆H₄-NHSO₂C₈H₁₇(n) |

-continued $R^1COCHCONHAr$
       |
       Z

| Coupler No. | $R^1$ | Z | Ar |
|---|---|---|---|
| (70) | 4-CH$_3$O-C$_6$H$_4$- | 4-(NHCO-CH$_2$CH$_2$CO$_2$H)-C$_6$H$_4$-O- | 4-Cl-3-CH$_3$-C$_6$H$_3$-CONH-C$_6$H$_4$-NHSO$_2$C$_8$H$_{17}$(n) |
| (71) | 4-CH$_3$O-C$_6$H$_4$- | 4-NO$_2$-C$_6$H$_4$-O- | 4-Cl-3-CH$_3$-C$_6$H$_3$-CONH-C$_6$H$_4$-OC$_{12}$H$_{25}$ |
| (72) | 4-CH$_3$O-C$_6$H$_4$- | 4-(CO$_2$-CH$_2$CH$_2$CO$_2$H)-C$_6$H$_4$-O- | 4-Cl-3-CH$_3$-C$_6$H$_3$-CONH-C$_6$H$_4$-OC$_{12}$H$_{25}$ |
| (73) | C$_6$H$_5$- | 4-NO$_2$-C$_6$H$_4$-O- | 4-Cl-3-CH$_3$-C$_6$H$_3$-CONHC$_{12}$H$_{25}$(n) |

-continued
| Coupler No. | R¹ | Z | Ar |
|---|---|---|---|
| (74) | 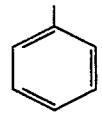 | 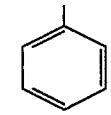 | 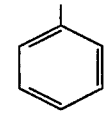 |
| (75) | 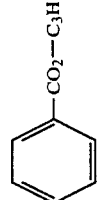 | 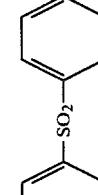 |  |
| (76) | 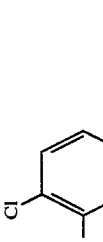 | 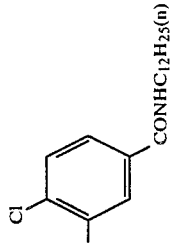 | 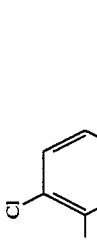 |
| (77) | 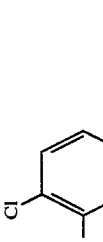 | 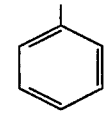 | 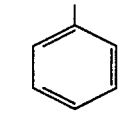 |
| (78) | 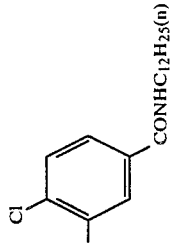 |  | 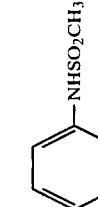 |
R¹COCHCONHAr
         |
         Z -continued
$R^1COCHCONHAr$
      $|$
      $Z$
| Coupler No. | $R^1$ | Z | Ar |
|---|---|---|---|
| (79) | 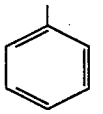 | 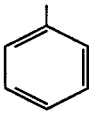 | 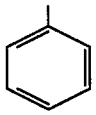 |
| (80) | 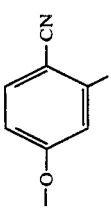 | 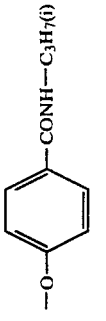 | 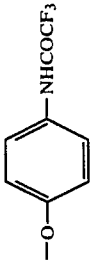 |
| (81) | 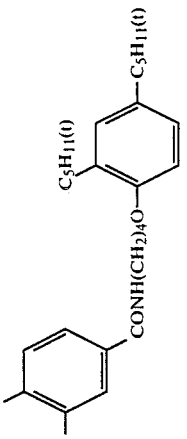 | 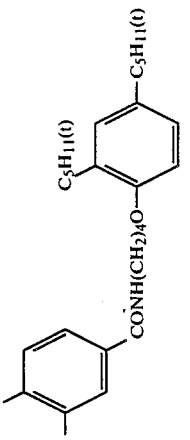 | 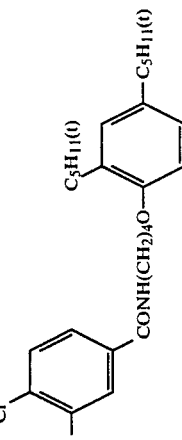 |
| (82) | 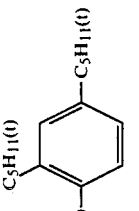 | 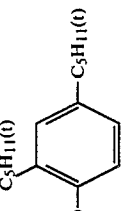 | 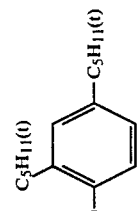 |

-continued
$R^1COCHCONHAr$
            $|$
            $Z$
| Coupler No. | $R^1$ | Z | Ar |
|---|---|---|---|
| (83) | 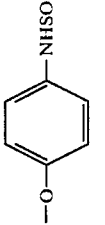 | 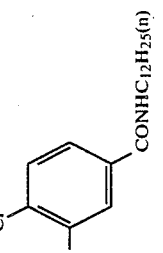 | 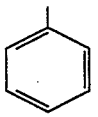 |
| (84) | 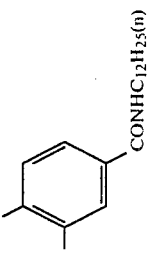 | 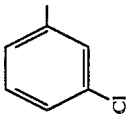 | 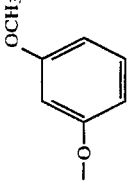 |
| (85) | 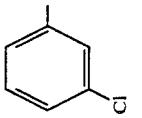 | 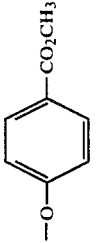 | 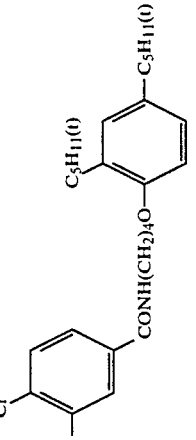 |
| (86) | 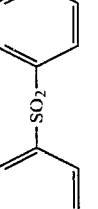 | 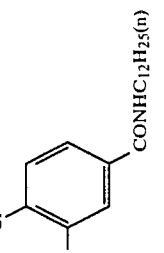 | 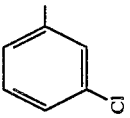 |
| (87) | 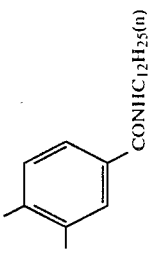 | 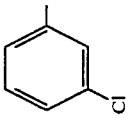 | 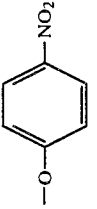 |

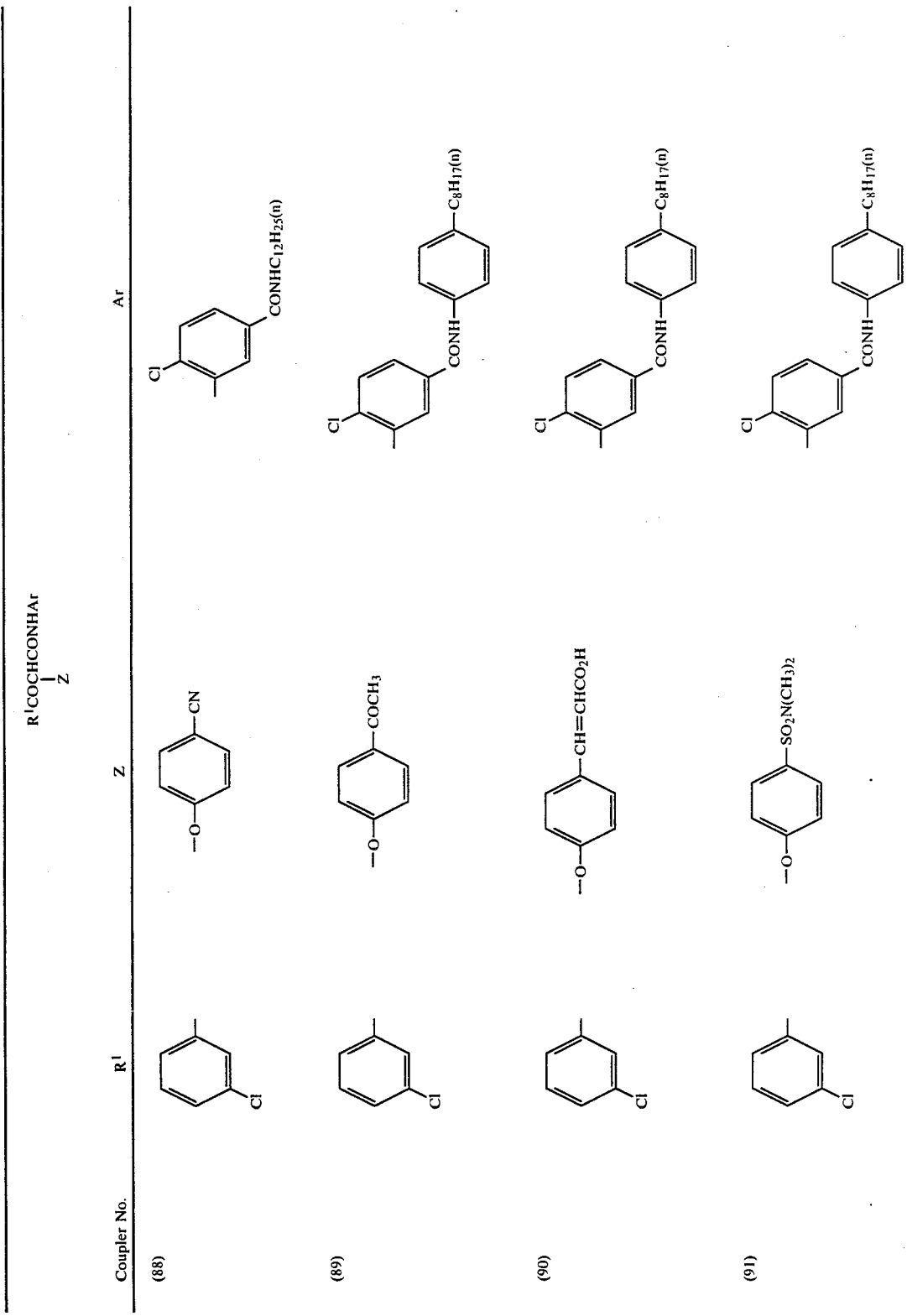

-continued $$R^1COCHCONHAr$$
$$\phantom{R^1COCH}|$$
$$\phantom{R^1COCHCO}Z$$

| Coupler No. | R¹ | Z | Ar |
|---|---|---|---|
| (92) | 3-Cl-C₆H₄– | 4-(C₃F₇CONH)-C₆H₄–O– | 4-Cl-3-CH₃-C₆H₃–CONH–C₆H₄-4-C₈H₁₇(n) |
| (93) | C₆H₅– | 2-(C₁₄H₂₉O)-C₆H₄–CONH–C₆H₄-4-O– | 3-CH₃-4-OCH₃-C₆H₃–CONHC₄H₉ |
| (94) | 4-CH₃O-C₆H₄– | 2-CH₃O-C₆H₄–SO₂NH–C₆H₄-4-O– | 3-CH₃-4-OCH₃-C₆H₃–CONHC₁₂H₂₅(n) |
| (95) | 4-CH₃O-C₆H₄– | 4-NO₂-C₆H₄–O– | 3-Cl-4-CH₃-C₆H₃–CONHC₁₆H₃₃(n) |
| (96) | C₆H₅– | 4-CH₃O₂C-C₆H₄–O– | 3-Cl-4-CH₃-C₆H₃–CONHC₁₆H₃₃(n) |

-continued $R^1COCHCONHAr$
$\phantom{R^1COCH}|$
$\phantom{R^1COCHCO}Z$

| Coupler No. | $R^1$ | Z | Ar |
|---|---|---|---|
| (97) | 3-O$_2$N-C$_6$H$_4$- | 4-CONH$_2$-C$_6$H$_4$-O- | 3-Cl-4-CH$_3$-C$_6$H$_3$-CONHC$_{16}$H$_{33}$(n) |
| (98) | 2-OCH$_3$-C$_6$H$_4$- | 4-CN-C$_6$H$_4$-O- | 3-Cl-4-CH$_3$-C$_6$H$_3$-CONHC$_{16}$H$_{33}$(n) |
| (99) | 2-OCH$_3$-C$_6$H$_4$- | 4-SO$_2$NHCH$_3$-C$_6$H$_4$-O- | 3-Cl-4-CH$_3$-C$_6$H$_3$-CONHC$_{16}$H$_{33}$(n) |
| (100) | 4-CH$_3$O-C$_6$H$_4$- | 4-NO$_2$-C$_6$H$_4$-O- | 4-Cl-3-CH$_3$-C$_6$H$_3$-CON(C$_8$H$_{17}$)$_2$ |
| (101) | 4-CH$_3$O-C$_6$H$_4$- | 4-CO$_2$CH$_3$-C$_6$H$_4$-O- | 4-Cl-3-CH$_3$-C$_6$H$_3$-CON(C$_8$H$_{17}$)$_2$ |

-continued
| Coupler No. | R¹ | Z | Ar |
|---|---|---|---|
| (102) | 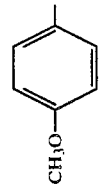 | 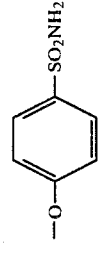 |  |
| (103) | 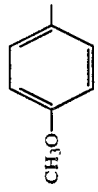 | 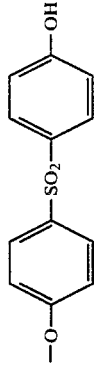 | 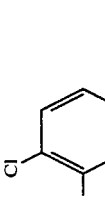 |
| (104) | 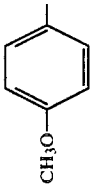 | 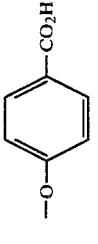 | 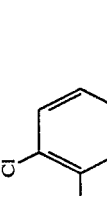 |
| (105) | 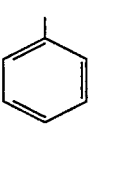 | 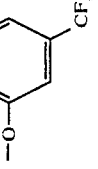 | 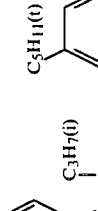 |
| (106) | 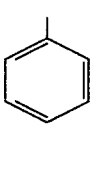 | 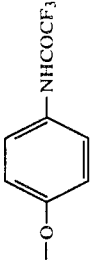 | 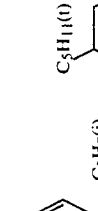 |

-continued $R^1COCHCONHAr$
$|$
$Z$

| Coupler No. | $R^1$ | Z | Ar |
|---|---|---|---|
| (107) | phenyl | 4-(4-methoxyphenoxy)phenoxy with OH | 3-methyl-4-methoxyphenyl-N(i-C3H7)CO-phenyl-C8H17(n) |
| (108) | 4-methoxyphenyl | 4-(propylcarbamoyl)phenoxy | 3-methyl-4-methoxyphenyl-N(i-C3H7)CO-phenyl-C8H17(n) |
| (109) | 4-methoxyphenyl | 4-sulfamoylphenoxy | 3-methyl-4-methoxyphenyl-N(i-C3H7)CO-phenyl-C8H17(n) |

The synthesis examples of the above-given couplers will now be described.

Synthesis Example-1 of Exemplified Coupler 1

Five grams of α-chloro-α-pivaloyl-2-chloro-5-dodecylcarbamoylavetanilide and 1.9 g of potassium 4-nitro phenoxide were dissolved in 100 ml of acetone, and the resulting solution was refluxed with heating for one hour. After completing the reflux, the acetone was distilled off under reduced pressure. The resulting dry-solid matter was dissolved in 200 ml of ethyl acetate and was then washed with 100 ml of an aqueous 5% potassium hydrogencarbonate solution three times and then with 100 ml of saturated sodium chloride solution once. After completing the washing, an organic solvent layer was separated and dehydrated with magnesium sulfate. Then, the solvents were removed therefrom under reduced pressure. The resulting dry-solid matter was recrystallized with 30 ml of ethanol, so that the subject exemplified coupler 1 could be obtained in a yield of 3.7 g and at a yield of 62%. The structure of the exemplified coupler 1 was then confirmed by an NMR, IR, and Mass spectrometry.

Synthesis Example-2 of Exemplified Coupler 62

α-chloro-α-(4-methoxybenzolyl)-2-chloro-5-(4-2,4-di-tertamylphenoxy]butylcarbamoyl)acetanilide of 6.7 g and 2.5 g of potassium 4-methylsulfonylaminophenoxide were dissolved in 100 ml of acetone. The resulting solution was refluxed with heating for one hour. After completing the reflux, a post-treatment was carried out in the same procedures as in Synthesis Example-1, so that the subject exemplified coupler 62 was obtained in a yield of 2.9 g and at a yield of 35%. The structure of the exemplified coupler 62 was confirmed by NMR, IR and Mass spectrometry.

The other couplers of the invention than the above were also synthesized by starting with the corresponding raw materials, similarly in the procedures described in Synthesis Examples-1 and 2.

The silver halide color photograhic light-sensitive material contains the above mentioned yellow coupler in at least one silver halide emulsion layer, preferably in at least one blue-sensitive emulsion layer, thereof.

The above-mentioned yellow couplers of the invention may be used independently or in combination and, further, any of known pivaloyl acetanilide type or benzolylacetanilide type yellow couplers may be jointly used.

In order that the yellow couplers of the invention are to be contained in the silver halide photographic emulsions of a color photographic light-sensitive material, the conventionally known methods therefor may be applied. For example, when the aforementioned protect-dispersion method is applied, the following procedures are taken. The yellow couplers of the invention are dissolved, independently or in combination, in any one of a high boiling organic solvent such as tricresyl phosphate or dibutyl phthalate having a boiling point of not lower than 175° C. and a low boiling organic solvent such as ethyl acetate and butyl propionate, independently or in the mixture thereof. The resulting solution is then mixed with an aqueous gelatin solution containing a surfactant. The resulting mixture is dispersively emulsified with a high speed rotary mixer or a colloid-mill. The resulting emulsified dispersion is added directly into the silver halide photographic emulsion. The resulting emulsified dispersion is coated over a support and dried, or the emulsified dispersion is set and cut into fine pieces. After the low boiling solvent is removed from the fine pieces by a means such as washing, the fine pieces are added into the emulsion and, with which a support may be coated.

In this case, it is generally preferable to add the yellow couplers of the invention in an amount within the range of 10 to 300 g per mol of silver halide used. It is, however, the matter of course that such an amount thereof to be added may be varied according to the purposes of applications.

Further, the coupler of the invention may also be used without being dissolved in the above-mentioned high boiling organic solvent, but with being dissoleved only in either a substantially water-insoluble low boiling organic solvent such as ethyl acetate and butyl acetate or water-soluable low boiling organic solvent such as methanol, ethanol, or methylcello-solve, and methylisobutylketone.

Any silver halide photographic light-sensitive materials may be applied to the invention, regardless of their kinds and purposes of use. For example, the invention may advantageously be applied particularly to multilayered negative type color photographic light-sensitive materials, photographic light-sensitive materials for color print use, or color photographic light-sensitive materials for reversal-color processing use.

The yellow couplers of the invention can also be used as those applicable to the so-called diffusion-transfer method in which a light sensitive element having a light-sensitive layer is brought into contact with a processing sheet for light-shielding so that a transfer image may be formed on the image-receiving layer of an image-receiving element.

Further, the yellow couplers of the invention can also be applied to the dye image forming methods described in, for example. Japanese Patent Examined Publication No. 49-26585(1974), U.S. Pat. No. 3,486,890, and Research Disclosure Nos. 12044 and 12840.

To be more concrete. a dye image having an excellent gradation can be obtained in the following manner. The yellow coupler of the invention and an aromatic primary amine developing agent or the precursor thereof are contained in a light-sensitive material. The light-sensitive material is exposed imagewise to light and is then color-developed by treating it either in an alkaline bath or by heating.

The color developing agents applicable for developing the color photographic light-sensitive material of the invention are aromatic primary amine type compounds include, typically, those of the p-aminophenol or p-phenylenediamine type. To be more concrete, they include, for example, p-aminophenol, diethyl-p phenylenediamine hydrochloride, monomethyl-p-phenylenediamine hydrochloride, dimethyl-p-phenylenediamine hydrochloride, 2-amino- β-diethylaminotoluene hydrochloride, 2-amino-β-(N-ethyl N-dodecylamino)-toluene, N-ethyl-N-β-methanesulfonamidethyl-3-methyl-4-aminoaniline sulfate, N ethyl-N-β-methanesulfonamidoethyl-4-aminoaniline, 4-N-ethyl-N-β-hydroxyethylaminoaniline, N-ethyl-N-β-methoxyethyl-3-methyl-4-aminoaniline.p-toluene sulfonate, N-ethyl-N-2-(2 methoxyethoxy)ethyl]-3-methyl-4-aminoaniline.p-toluene sulfonate, and N-ethyl-N-(Z 2-methoxyethoxy)ethoxy)ethyl)-3-methyl 4-aminoaniline.p-toluene sulfonate.

The above-mentioned color developing agents are used independently or in combination. In the invention, color developers are allowed to contain any of the various components generally added thereto, including, for example, alkalizers such as sodium hydroxide, sodium carbonate, and potassium carbonate, alkali-metal sulfites, alkali-metal bysulfites, alkali-metal thiocyanates, alkali-metal halides, benzyl alcohol, a water-softener, a thickener, and development controllers such as citrazinic acid.

The pH value of this kind of color developers is, usually, not lower than 7 and, most generally, within the range of about 10 to about 13.

In reversal processing of the color photographic light-sensitive material of the invention, a black-and-white development may be used with a color development.

In the processing of the color photographic material of invention, after completing a development step with a color developer, any steps may follow on, such as a bleaching, fixing, bleach-fixing, stabilizing, washing, or stopping step.

The silver halides used in this case include, for example, silver chloride, silver bromide, siver iodide, silver chlrobromide, silver iodobromide, and silver chloroiodobromide. The silver halide emulsions may be prepared in any one of the well-known methods. Such silver halide emulsions may be the so-called conversion type emulsions, Lippman type emulsions, coverd-grain type emulsions, or the emulsions either optically or chemically fogged in advance. These emulsions may be suitably selected to meetthe kinds and purposes of the use of photographic light-sensitive materials. Similarly to the above, the kinds, contents, mixing ratios, average grain-sizes and grain-size distributions of silver halides are suitably selected to meet the kinds and purposes of photographic light-sensitive materials to be used.

These silver halides may also be chemically sensitized by making use of the following sensitizers independently or in combination of, for example, gold and sulfur senstizers or gold and selenium sensitizer; namely, active gelatin; a sulfur sensitizer such as thiosulfates allylthiocarbamide, thiourea, and cystine; a selenium sensitizer; a reduction sensitizer such as stannous salts and polyamines; or a noble-metal sensitizer including, for example, a gold sensitizer such as potassium aurithiocyanate, potassium chloroaurate, and 2-aurosulfobenzothiazole, a sensitizer of such a water-soluble salts such as those of ruthenium, rhodium, and iridium and, more concretely, ammonium chloropalladate, potassium chloroplatinate, and sodium chloroparamide, -Some kinds of them may serve as a sensitizer or an antifoggant, it all depends on the amounts thereof used.

The above-mentioned silver halides may be optically sensitized or super-sensitized to a desired wavelength region by making independent or combination use of optical sensitizers including, for example, cyanine or merocyanine dyes such as zeromethine, monomethine dimethine and trimethine dyes.

These silver halides are dispersed in a suitable protective colloid so as to constitute a light-sensitive layer.

Such protective colloids are applicable to the layer arrangements of the light-sensitive layers and the other component layers such as an interlayer, a protective layer, and a filter layer. Such protective colloids include, for example, alkali-pretreated gelatin for general use and, besides, acid-pretreated gelatin, derivative gelatin, colloidal albumin, cellulose derivative, or synthetic resins such as polyvinyl compounds, e.g., polyvinyl alcohol. They may be used independently or in combination. Further, acetyl cellulose having an acetyl content of the order within the range of 19 to 26% or a water-sluble ethanolamine cellulose acetate may also be used in combination.

Into the silver halide photographic light-sensitive materials relating to the invention, the yellow couplers of the invention and the other color couplers may be contained so as to form multicolor images. It is also allowed to use an azo type colored coupler, an osazone type compound, and a dispersible dye releasing type coupler in combination with the above-given couplers so as to apply an automasking. In this instance, it is desirable to use a desired colorless coupler that is colorless before a color development is made and the above-mentioned masking coupler in combination. It is, further, allowed to contain a variety of couplers including, for example, the so-called completing couplers, DIR couplers, and Bleach Accelerator Releasing- coupler(-BAR coupler) so as to improve photographic characteristics.

The magenta couplers capable of being used, in the invention, jointly with the yellow couplers of the invention include, for example, the compounds of the pyrazolone, pyrazolotriazole, pyrazolinobenzimidazole, and indazolone types.

The cyan couplers capable of being used jointly with the yellow couplers of the invention include, for example, a phenol compound, and a naphthol compound.

A silver halide photographic light-sensitive material applied with the invention can be prepared by providing onto a support with a silver halide emulsion layer containing the yellow coupler of the invention thus prepared together with, if required, a subbed layer, an interlayer, a filter layer, a curl control layer, and a protective layer. The supports applicable thereto include, for example, a sheet of paper, laminated paper such as a polyethylene-laminated paper, a glass plate, and a film or sheet comprising a substrate such as cellulose acetate, cellulose nitrate, polyester, polycarbonate, polyamide, polystyrene or polyolefin. These supports may be surface-treated in various hydrophilic treatments including, for example, a saponification treatment, a corona-discharge treatment, a subbing treatment, and a setting treatment, with the purpose of improving the adhesion of the support to each component layer.

Basically, the silver halide photographic light-sensitive material relating to the invention comrises at least a support bearing thereon a light-sensitive layer. It is, however, usual to comprise a plurality of suitable layers in various positions as the purposes demand. Such light-sensitive layer itself may have a multilayered constitution in which, for example, one layer containing a relatively higher sensitive silver halide and the other layer containing a relatively lower sensitive silver halide are superposed together to make them color-sensitive to the same or different wavelength region.

In the silver halide photograpic light-sensitive material relating to the invention, a variety of additives may be added to the light-sensitive layers and/or the component layers such as an inter layer, a subbing layer, a filter layer, a protective layer, and an image-receiving layer, so as to meet the purposes of using the light-sensitive materials. Such photographic additives include, for example, stabilizers such as mercury compounds, triazoles, azaindenes, quaternary benzothiazolium, zincsalts, or cadmiumsalts; sensitizers such as quaternary ammonium salts, and polyethylene glycols; Physical property improving agents such as glycerol, 1,5-pentadiol, dihydroxyalkane, ethylenebisglycolic acid esters, bisethoxydiethyleneglycol succinate, acrylic acid amides, and the emulsified dispersions of polymers, hardeners such as formaldehyde, halogen-substituted aliphatic acids, e.g., mucochloric acid and mucobromic acid, compounds having acid anhydride group, dicarboxylic acid chloride, disulfonic acid chloride, methanesulfonic acid biesters, sodium bisulfite derivatives of dialdehyde whose aldehyde group is separated therefrom by 2 or 3 carbon atoms, bisaziridine, and ethyleneimines; spreading agents such as saponin, lauryl or oleyl monoether of polyethylene glycol, and sulfated or alkylated polyethylene glycol salts sulfosuccinates; organic solvents including, for example, coupler solvents such as high and/or low boiling organic solvents and, more concretely, dibutyl phthalate, tricresyl phosphate, acetone, methanol, ethanol, and ethylcellosolve; the so-called DIR compounds capable of releasing a color development inhibitor when a color developing step is carried out and at the same time producing a substantial colorless compound; besides, an antistatic agent; a defoaming agent; a UV absorver; a fluorescent brightening agent; an antislipping agent; a matting agent; an antihalation agent; and an anti-irradiation agent. These photographic additives may be used independently or in combination.

When a UV absorber is added into the silver halide photographic light-sensitive materials containing the yellow coupler of the invention, yellow image durability can further be improved.

EXAMPLES

Next, the invention will be more detailed with reference to the examples thereof. It is, however, to be understood that the emobodiments of the invention shall not be limited thereto.

In the examples, the following couplers were used for the comparison.

Coupler described in Japanese Patent O.P.I.
Publication No. 63-43144(1988)

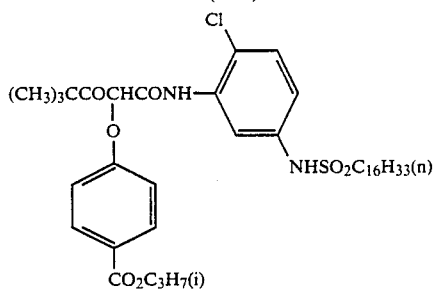

Y-1

Coupler described in Japanese Patent O.P.I.
Publication No. 62-153954(1987)

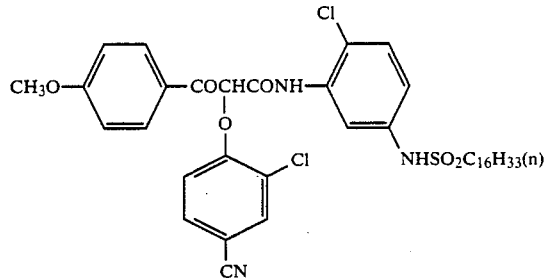

Y-2

Coupler described in Japanese Patent O.P.I.
Publication No. 62-250446(1987)

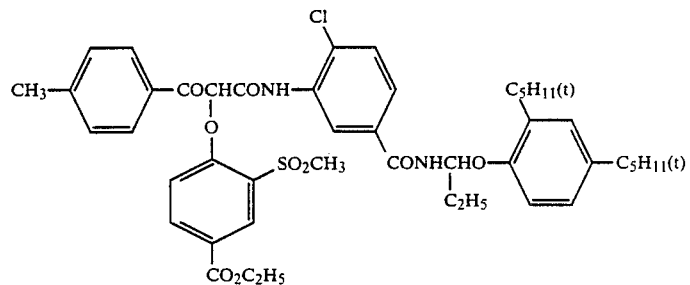

Y-3

Coupler described in U.S. Patent No. 4,401,752

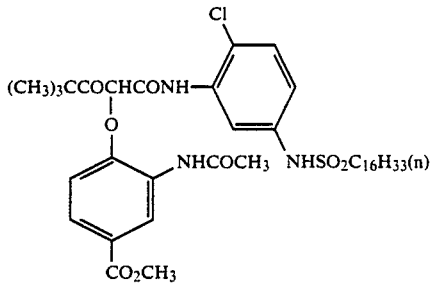

Y-4

EXAMPLE-1

As shown in Table 1 below, 10.0 g each of the yellow couplers of the invention corresponding to the foregoing exemplified coupler number and 10.0 g each of the above-given comparative couplers were added into the mixtures each of 2.0 ml of dibutyl phthalate and 20 ml of ethyl acetate, and dissolved together with heating at 50° C., respectively.

The resulting solutions were each mixed with 5 ml of a 10% aqueous solution of alkylnaphthalene sulfonate, Alkanol B manufactured by DuPont, and 100 ml of a 5% aqueous solution of gelatin, respectively. The resulting mixtures were each emulsified through a colloid-mill several time. After the emulsification, the emulsions were each stored for 48 hours at 20° C. and were then observed with the naked eye through a 20X-magnifier. The results thereof are shown in Table 1.

TABLE I

| Sample No. | Coupler No. | Condition after stored |
|---|---|---|
| 1 Invention | (2) | No deposition found |
| 2 Invention | (10) | No deposition found |
| 3 Invention | (14) | No deposition found |
| 4 Invention | (23) | No deposition found |
| 5 Invention | (56) | No deposition found |
| 6 Invention | (64) | No deposition found |
| 7 Invention | (77) | No deposition found |
| 8 Invention | (101) | No deposition found |
| 9 Comparative | Y-1 | No deposition found |
| 10 Comparative | Y-2 | Deposited a little |
| 11 Comparative | Y-3 | Deposited markedly |
| 12 Comparative | Y-4 | Deoosited markedly |

As is obvious from Table 1 above, it was found that every yellow coupler of the invention did not produce any deposition and is excellent in dispersion stability even when the emulsions were stored on standing.

EXAMPLE-2

Multilayered color paper sample 13 was prepared by applying a coronadischarge treatment onto a support coated with polyethylene on the both sides thereof and then by coating the following seven layers thereon in order from the support side. The amounts coated will be expressed in terms of those coated per sq. meter, unless otherwise expressly stated.

Layer 1: A layer containing 1.5 g of gelatin, 0.33 g -in terms of the silver content- of blue-sensitive silver chlorobromide emulsion having a silver bromide content of 85 mol% and an average grain-size of 0.65 μm, and 0.25 g of dioctyl phthalate dissolved therein $1.1 \times 10^{-3}$ mols of exemplified yellow coupler 2 and 0.015 g of the following HQ-1.

Layer 2: A layer containing 1.0 g of gelatin and 0.06 g of dioctyl phthalate dissolved therein 0.09 g of HQ-1.

Layer 3: A layer containing 1.3 g of gelatin, 0.27 g -in terms of the silver content- of green-sensitive silver chlorobromide emulsion having a silver bromide content of 50 mol% and an average grain-size of 0.45 μm, 0.2 g of dioctyl phthalate dissolved therein $0.59 \times 10^{-3}$ mols of the following magenta coupler M-1 and 0.015 g of HQ-1, and 0.15 g of the following anti-irradiation dye AID-1.

Layer 4: A layer containing 1.5 g of gelatin, and 0.6 g of dioctyl phthalate dissolved therein 0.8 g of UV absorbent UV-1 and 0.04 g of HQ-1.

Layer 5: A layer containing 1.3 g of gelatin, 0.3 g -in terms of the silver content- of red-sensitive silver chlorobromide emulsion having a silver bromide content of 50 mol% and an average grain-size of 0.35 μm, and 0.2 g of dioctyl phthalate dissolved therein $0.75 \times 10^{-3}$ mols of the following cyan coupler C-1 and 0.005 g of HQ-1.

Layer 6: A layer containing 1.0 g of gelatin, and 0.015 g of dioctyl phthalate dissolved therein 0.4 g of UV absorbent and 0.01 g of HQ-1.

Layer 7: A layer containing 1.0 g of gelatin, and 0.015 g of the following filter dye AID-2.

In this sample, the dispersing solutions of the couplers were each used after keeping them for 8 hours at 40° C. upon completing the dispersion.

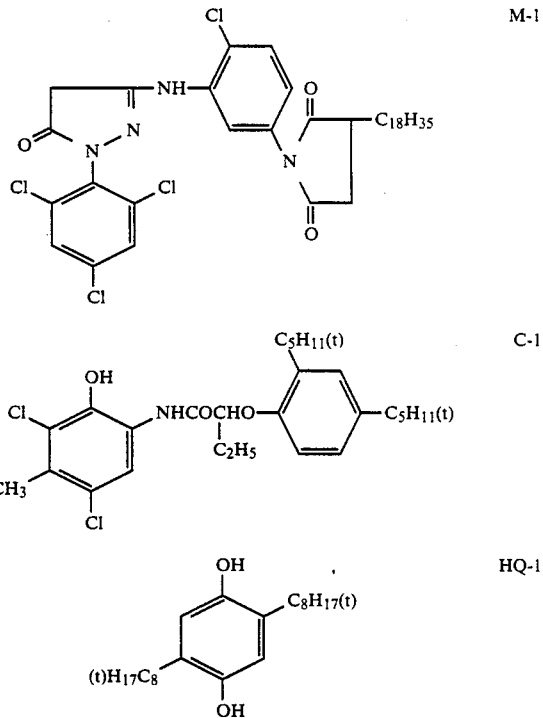

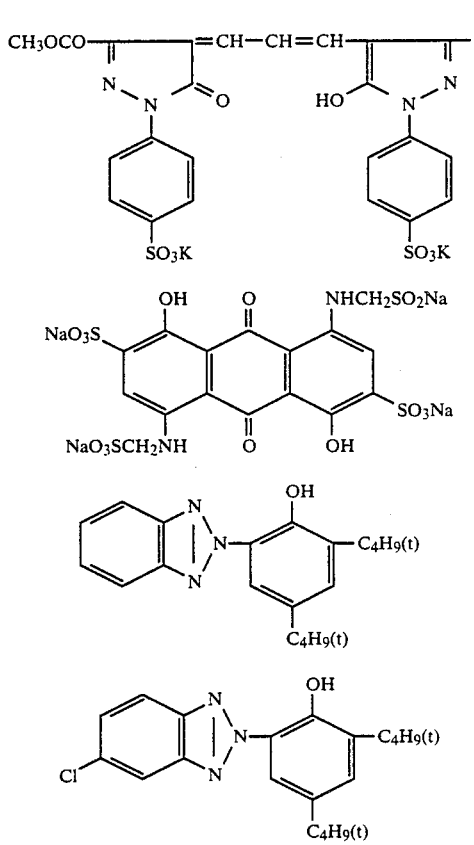

Samples 14 through 23 were each prepared in the same manner as in Sample 13, except that he coupler of Layer 1 of Sample 13 was replaced by those, respectively, shown in Table 2 below. These samples were each exposed wedgewise to light in an ordinary method and processed in the processing steps with the processing solutions given below. The results thereof are shown in Table 2.

| Processing steps: | |
| --- | --- |
| Color developing | 3 min. 30 sec. |
| Bleach-fixing | 1 min. 30 sec. |
| Washing | 2 min. 0 sec. |
| Stabilizing | 1 min. 0 sec. |
| Color developer A: | |
| Benzyl alcohol | 15 ml |
| Sodium hexametaphosphate | 3.00 g |
| Sodium sulfite, anhydrous | 1.85 g |
| Sodium bromide | 1.40 g |
| Potassium bromide | 0.50 g |
| Boric acid, $Na_2B_4O_7.10H_2O$ | 39.10 g |
| N-ethyl-N-[2-(methanesulfon amidoethyl)]-3-methyl-4-aminoaniline sulfate | 4.50 g |
| Add water to make | 1 liter |

Adjust pH with sodium hydroxide to pH 10.3 Color Developer B:

This developer was prepared in the same manner as in Developer A, except that benzyl alcohol was not used. Bleach-fixer:

| Bleach-fixer: | |
| --- | --- |
| Ferric-ammonium ethylene-diaminetetraacetate | 61.0 g |
| Diammonium ethylene-diaminetetraacetate | 5.0 g |
| Ammonium thiosulfate | 124.5 g |
| Sodium metabisulfite | 13.3 g |
| Sodium bisulfite | 2.7 g |
| Add water to make | 1 liter |
| Adjust pH to be | pH 6.5 |
| Stabilizer: | |
| Glacial acetic acid | 20 ml |
| Pure water | 800 ml |
| Adjust pH with sodium acetate trihydrate to be | pH 3.5 to 4.0 |
| Make the total amount to be | 1 liter |

Table 2 shows the results of the dye images obtained after the samples were processed.

TABLE 2

| Sample No. | Coupler No. | Maxixum density | | | | | |
| --- | --- | --- | --- | --- | --- | --- | --- |
| | | Developer A | | | Developer B | | |
| | | Yellow | Magenta | Cyan | Yellow | Magenta | Cyan |
| 13 Invention | (2) | 2.41 | 2.63 | 2.60 | 2.30 | 2.54 | 2.36 |
| 14 Invention | (10) | 2.43 | 2.60 | 2.57 | 2.30 | 2.52 | 2.37 |
| 15 Invention | (14) | 2.45 | 2.62 | 2.56 | 2.32 | 2.55 | 2.35 |
| 16 Invention | (23) | 2.40 | 2.61 | 2.59 | 2.28 | 2.51 | 2.38 |
| 17 Invention | (40) | 2.41 | 2.63 | 2.61 | 2.28 | 2.53 | 2.37 |
| 18 Invention | (56) | 2.48 | 2.63 | 2.59 | 2.35 | 2.54 | 2.36 |
| 19 Invention | (64) | 2.49 | 2.59 | 2.58 | 2.34 | 2.56 | 2.34 |
| 20 Comparative | Y-1 | 1.98 | 2.60 | 2.60 | 1.72 | 2.55 | 2.39 |
| 21 Comparative | Y-2 | 2.28 | 2.61 | 2.62 | 2.15 | 2.51 | 2.35 |
| 22 Comparative | Y-3 | 2.39 | 2.62 | 2.58 | 2.25 | 2.50 | 2.38 |
| 23 Comparative | Y-4 | 2.09 | 2.62 | 2.60 | 1.99 | 2.53 | 2.36 |

As is obvious from Table 2 above, with the yellow couplers of the invention, a maximum density was little lowered and the color balance was excellent as compared to the comparative couplers, even when the samples were developed with developer B from which benzyl alcohol was removed.

EXAMPLE-3

Each of the layers having the following composition was coated over a triacetyl cellulose film support in order from the support side, so that multilayered color photographic element sample 24 was prepared.

Layer 1: An antihalation layer HC1, i.e., a gelatin layer containing black colloidal silver.

Layer 2: An interlayer I.L., i.e., a gelatin layer containing the emulsified dispersion of 2,5-di-t-octyl hydroquinone.

Layer 3: A low-speed red-sensitive silver halide emulsion layer RL-1, i.e., a layer containing the following components:

A monodispersed AgBrI emulsion, Em-I, having an average grain-size r of 0.30 μm and an AgI content of 6 mol%.
Amount of the emulsion coated: 1.8 g/m² in terms of the silver content
Sensitizing dye I 6×10⁻⁵ mols per mol of silver
Sensitizing dye II 1.0×10⁻⁵ mols per mol of silver
Cyan coupler C-2 0.06 mols per mol of silver
Colored cyan coupler CC-1 0.003 mols per mol of silver
DIR compound D-1 0.0015 mols per mol of silver
DIR compound D-2 0.002 mols per mol of silver Layer 4: A high-speed red-sensitive silver halide emulsion layer RH-1, i.e., a layer containing the following components:

A monodispersed AgBrI emulsion, Em-II, having an average grain-size r of 0.5 μm and an AgI content of 7.0 mol%.
Amount of the emulsion coated: 1.3 g/m² in terms of the silver content
Sensitizing dye I 3×10⁻⁵ mols per mol of silver
Sensitizing dye II 1.0×10⁻⁵ mols per mol of silver
Cyan coupler C-2 0.002 mols per mol of silver
Colored cyan coupler CC-1 0.0015 mols per mol of silver
DIR compound D-2 0.001 mol per mol of silver Layer 5: An interlayer I.L., i.e., the same gelatin layer as Layer 2

Layer 6: A low-speed green-sensitive silver halide emulsion layer GL-1
Emulsion I Amount thereof coated: 1.5 g/m² in terms of the silver content
Sensitizing dye III 2.5×10⁻⁵ mols per mol of silver
Sensitizing dye IV 1.2×10⁻⁵ mols per mol of silver
Magenta coupler M-2 0.050 mols per mol of silver
Colored magenta coupler CM-1 0.009 mols per mol of silver
DIR compound D-1 0.0010 mol per mol of silver
DIR compound D-3 0.0030 mols per mol of silver Layer 7: A high-speed green-sensitive silver halide emulsion layer GH-1
Emulsion II: Amount of the emulsion coated 1.4 g/m² in terms of silver coated.
Sensitizing dye III 1.5×10⁻⁵ mols per mol of silver
Sensitizing dye IV 1.0×10⁻⁵ mols per mol of silver
Magenta coupler M-2 0.020 mols per mol of silver
Colored magenta coupler CM-1 0.002 mols per mol of silver
DIR compound D-3 0.0010 mol of silver Layer 8: A yellow filter layer YC-1, i.e., a gelatin layer containing an emulsified dispersion of yellow colloidal silver and 2,5-di-t-octyl hydroquinone Layer 9: A low-speed blue-sensitive silver halide emulsion layer BL-1

Emulsion III, i.e., a monodispersed AgBrI emulsion having an average grain-size r̄ of 0.48 μm and an AgI content of 6 mol%
Amount of the emulsion coated: 0.9 g/m² in terms of silver coated
Sensitizing dye V 1.3×10⁻⁵ mols per mol of silver
Comparative yellow coupler Y-1 0.29 mols per mol of silver
Tricresyl phosphate 0.7 ml/m²

Layer 10: A high-speed blue-sensitive silver halide emulsion layer BH-1
Emulsion IV, a monodispersed AgBrI emulsion having an average grain-size r̄ of 0.8 μm and an AgI content of 15 mol%
Amount of the emulsion coated: 0.5 g/m² in terms of silver
Sensitizing dye V 1.0×10⁻⁵ mols per mol of silver
Comparative yellow coupler Y-1 0.08 mols per mol of silver
DIR compound D-2 0.0015 mols per mol of silver
Tricresyl phosphate 0.2 ml/m²

Layer 11: The first protective layer Pro1, i.e., a gelatin layer containing silver iodobromide having an average grain-size r̄ of 0.07 μm and an AgI content of 1 mol%, coated in an amount of 0.5 g/m² in terms of silver, and UV absorbents UV-3 and UV-4.

Layer 12: The second protective layer Pro-2, i.e., a gelatin layer containing polymethyl methacrylate particles having a particle-size of 1.5 μm, and formalin scavenger HS-1

Into each of the layers, a gelatin hardener H-1 and a surfactant were added, besides the above-given compositions.

Each layer of Sample 24 contained the following compounds.

Sensitizing Dye I

Anhydro 5,5'-dichloro-9-ethyl-3,3'-di-(3-sulfo propyl)thiacarbocyanine hydroxide Sensitizing Dye II Anhydro 9-ethyl-3,3'-di-(3-sulfopropyl)-4,5,4',5'-dibenzothiacarbocyanine hydroxide Sensitizing Dye III Anhydro 5,5'-diphenyl-9-ethyl-3,3'-di-(3-sulfo propyl)oxacarbocyanine hydroxide Sensitizing Dye IV Anhydro 9-ethyl-3,3'-di-(3-sulfopropyl)-5,6,5', 6'-dibenzooxacarbocyanine hydroxide Sensitizing Dye V Anhydro 3,3'-di-(3-sulfopropyl)-4,5-benzo-5'-methoxythiacyanine

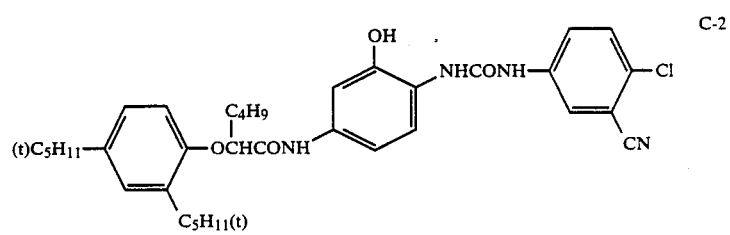

CC-1
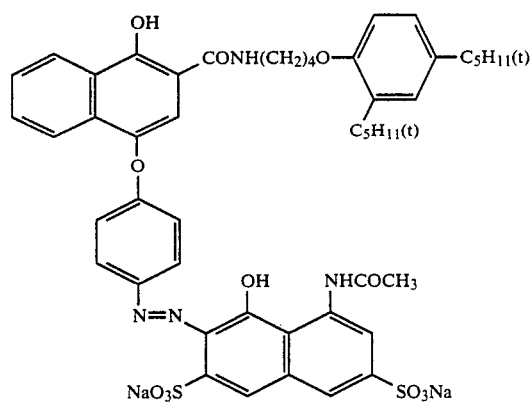
D-1
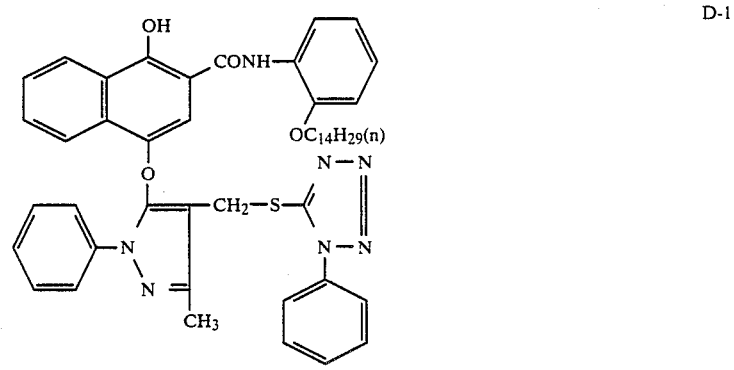
D-2
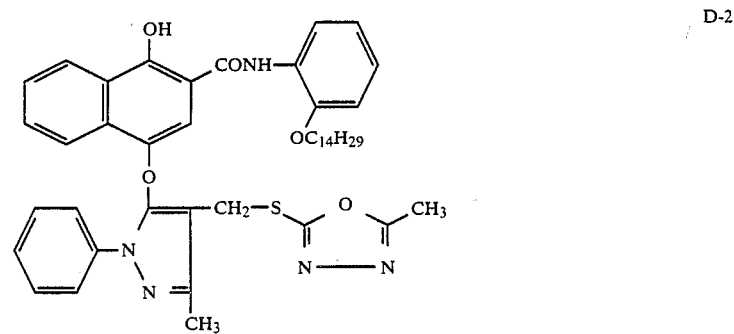
D-3
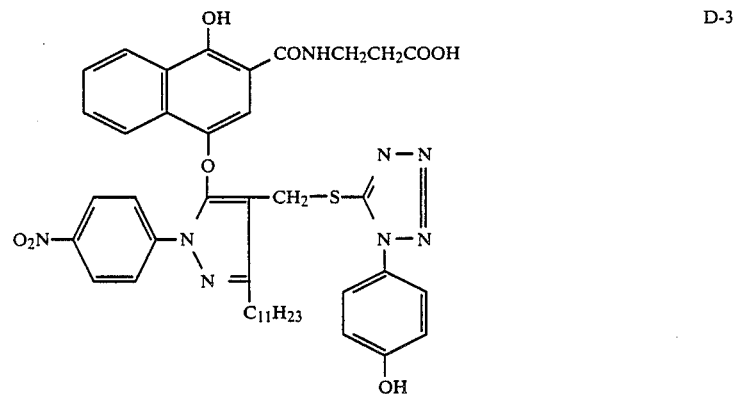
M-2
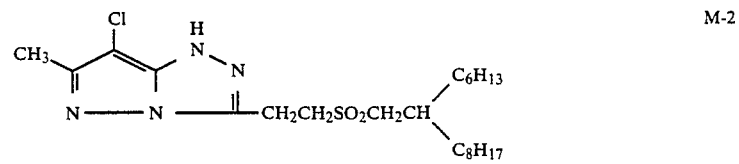

CM-1

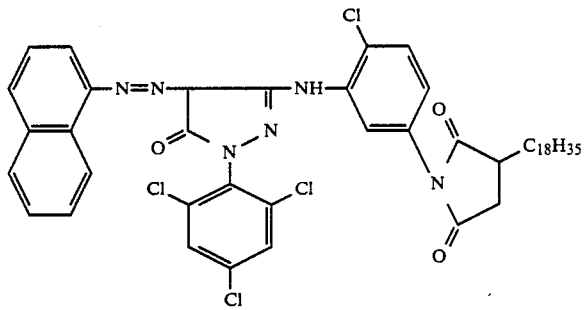

UV-3

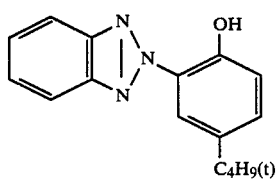

UV-4

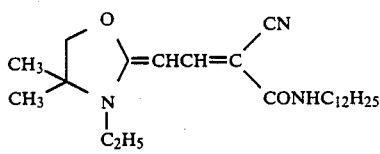

HS-1

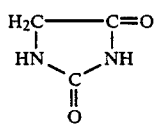

H-1

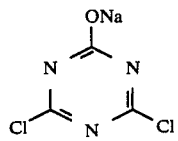

Samples 25 through 33 were prepared by changing Comparative Coupler Y-1 of Layers 9 and 10 of Sample 24 to those shown in Table 3.

The samples thus prepared were exposed wedgewise to light in an ordinary method and processed in the following processing steps and by making use of the following processing solutions.

The densities of the processed samples were measured through a blue filter. The results thereof are shown in Table 3, below.

Processing Steps

| Color developing at 38° C. | 3 min. 15 sec. |
|---|---|
| Bleaching at 38° C. | 6 min. 30 sec. |
| Washing at 38° C. | 3 min. 15 sec. |
| Fixing at 38° C. | 6 min. 30 sec. |
| Washing at 38° C. | 3 min. 15 sec. |
| Stabilizing at 38° C. | 1 min. 30 sec. |
| Drying | |

The processing solutions used in the processing steps have the following compositions.

Color Developer

| Color developer | |
|---|---|
| 4-amino-3-methyl-N-ethyl-N-(β- | 4.75 g |

-continued

| hydroxyethyl)-aniline sulfate | |
|---|---|
| Sodium sulfite, anhydrous | 4.25 g |
| Hydroxylamine.½ sulfate | 2.0 g |
| Potassium carbonate, anhydrous | 37.5 g |
| Sodium bromide | 1.3 g |
| Trisodium nitrilotriacetate, monohydrate | 2.5 g |
| Potassium hydroxide | 1.0 g |
| Add water to make | 1 liter |
| Bleaching solution | |
| Ferric-ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| Add water to make | 1 liter |
| Adjust pH with aqueous ammonia to | pH = 6.0 |
| Fixer | |
| Ammonium thiosulfate | 175 g |
| Sodium sulfite, anhydrous | 8.5 g |
| Sodium metasulfite | 2.3 g |
| Add water to make | 1 liter |
| Adjust pH with acetic acid to | pH = 6.0 |
| Stabilizer | |
| Formalin in an aqueous 37% solution | 1.5 ml |
| Konidux, manufactured by KONICA CORP. | 7.5 ml |
| Add water to make | 1 liter |

TABLE 3

| Sample No. | Coupler No. | ΔFog*[1] | Maximum density | Relative sensitivity*[2] |
|---|---|---|---|---|
| 24 Comparative | Y-1 | ±0 | 2.22 | 100 |
| 25 Comparative | Y-2 | +0.03 | 2.32 | 104 |
| 26 Comparative | Y-3 | +0.06 | 2.36 | 106 |
| 27 Comparative | Y-4 | +0.03 | 2.25 | 101 |
| 28 Invention | (2) | +0.02 | 2.42 | 114 |
| 29 Invention | (55) | +0.03 | 2.46 | 116 |
| 30 Invention | (64) | +0.02 | 2.46 | 115 |
| 31 Invention | (77) | +0.04 | 2.53 | 121 |
| 32 Invention | (79) | +0.02 | 2.49 | 118 |
| 33 Invention | (101) | +0.02 | 2.48 | 117 |

*[1]Fog difference between each sanmple and Sample 24
*[2]Sensitivity values of samples each relative to that of Sample 24 regarded as a value of 100

As is obvious from Table 3 above, it was found that the yellow couplers of the invention can improve both density and sensitivity without increasing fog.

EXAMPLE-4

Samples 34 through 39 each were prepared in the same manner as in Samples 24, 26, 29, and 31 through 33, except that the quantities of the yellow coupler and tricresyl phosphate is varied keeping the quantitative proportion of them to constant so as the color densities of the samples to be the same. The resulting samples were exposed to white light through an MTF-measuring pattern and were then processed in the same manner as in Example-3. After completing the processing them, Using blue rays of light, the MTF values of these samples were measured with a spatial frequency of 20 cycles/mm so as to evaluate the sharpness of the samples. The results thereof are shown in Table 4, below.

TABLE 4

| Sample No. | Coupler No. | MTF value* |
|---|---|---|
| 34 Comparative | Y-1 | 100 |
| 35 Comparative | Y-3 | 106 |
| 36 Invention | (55) | 112 |
| 37 Invention | (77) | 118 |
| 38 Invention | (79) | 116 |
| 39 Invention | (101) | 117 |

*MTF values each relative to that of Sample 34 regarded as a value of 100

As is obvious from Table 4 above, it was found that the yellow couplers of the invention can effectively improve the sharpness of images.

EXAMPLE-5

Each of the layers having the following compositions were coated over a subbed triacetyl cellulose film support in order from the support side, so that multilayered color light-sensitive material sample 40 was prepared as a comparative sample. In the sample, the amounts of the components thereof will be expressed in terms of gram per sq. meter. The amounts of the silver halide emulsions will be expressed in terms of gram of silver per sq. meter. And the amounts of coupler will be expressed in terms of mols per mol of silver contained in the layer.

| Layer I: An antihalation layer | |
|---|---|
| UV absorbent U-1 | 0.3 |
| UV absorbent U-2 | 0.4 |
| High boiling solvent O-1 | 1.0 |
| Black colloidal silver | 0.24 |
| Gelatin | 2.0 |
| Layer 2: An interlayer | |
| 2,5-di-t-octyl hydroquinone | 0.1 |
| High boiling solvent O-1 | 0.2 |
| Gelatin | 1.0 |
| Layer 3: A high-speed red-sensitive silver halide emulsion layer | |
| AgBrI emulsion spectrally sensitized with red-sensitizing dyes S-1, S-2, having an AgI content of 4.0 mol % and an average grain-size of 0.2 μm | 0.5 |
| Coupler C-1 | 0.1 |
| High boiling solvent O-2 | 0.6 |
| Gelatin | 1.3 |
| Layer 4: A high-speed red-sensitive silver halide emulsion layer | |
| AgBrI emulsion spectrally sensitized with red-sensitizing dyes S-1, S-2, having an AgI content of 2 mol % and an average grain-size of 0.6 μm | 0.8 |
| Coupler C-1 | 0.2 |
| High boiling solvent O-2 | 1.2 |
| Gelatin | 1.8 |
| Layer 5: An interlayer | |
| 2,5-di-t-octyl hydroquinone | 0.1 |
| High boiling solvent O-1 | 0.2 |
| Gelatin | 0.9 |
| Layer 6: A low-speed green-sensitive silver halide emulsion layer | |
| AgBrI emulsion spectrally sensitized with green-sensitizers S-3, S-4, having an AgI content of 4 mol % and an average grain-size of 0.2 μm | 0.6 |
| Coupler C-2 | 0.04 |
| Coupler C-3 | 0.01 |
| High boiling solvent O-3 | 0.5 |
| Gelatin | 1.4 |
| Layer 7: A high-speed green-sensitive silver halide emulsion layer | |
| AgBrI emulsion spectrally sensitized with green-sensitizers S-3, S-4, having an AgI content of 2 mol % and an average grain-size of 0.6 μm | 0.9 |
| Coupler C-2 | 0.10 |
| Coupler C-3 | 0.02 |
| High boiling solvent O-3 | 1.0 |
| Gelatin | 1.5 |
| Layer 8: An interlayer Same as Layer 5 | |
| Layer 9: A yellow filter layer | |
| Yellow colloidal silver | 0.1 |
| Gelatin | 0.9 |
| 2,5-di-t-octyl hydroquinone | 0.1 |
| High boiling solvent O-1 | 0.2 |
| Layer 10: A low-speed blue-sensitive silver halide emulsion layer | |
| AgBrI emulsion spectrally sensitized with blue-sensitizers S-5, having an AgI content of 4 mol % and an average grain-size of 0.35 μm | 0.6 |
| Comparative Coupler Y-1 | 0.3 |
| High boiling solvent O-3 | 0.6 |
| Gelatin | 1.3 |
| Layer 11: A high-speed blue-sensitive silver halide emulsion layer | |
| AgBrI emulsion spectrally sensitized with blue-sensitizers S-5, having an AgI content of 2 mol % and an average grain-size of 0.9 μm | 0.9 |
| Comparative Coupler Y-1 | 0.5 |
| High boiling solvent O-3 | 1.4 |
| Gelatin | 2.1 |
| Layer 12: The first protective layer | |
| UV absorbent U-1 | 0.3 |
| UV absorbent U-2 | 0.4 |
| High boiling solvent O-3 | 0.6 |
| Gelatin | 1.2 |
| 2,5-di-t-octyl hydroquinone | 0.1 |
| Layer 13: The second protective layer | |
| A non-light-sensitive fine-grained silver iodobromide emulsion having an average grain-size of 0.08 μm and a silver iodide content of 1 mol % in terms of the | 0.3 |

| -continued | |
|---|---|
| silver content | |
| Polymethyl methacrylate particle having a diameter of 1.5 μm | |
| Surfactant-1 | |

| -continued | |
|---|---|
| Gelatin | 0.7 |

Further to each of the layers, the other additives such as a gelatin hardener-1 and a surfactant were added, besides the above-given compositions.

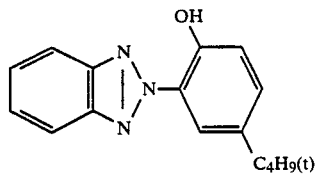

UV absorbent U-1

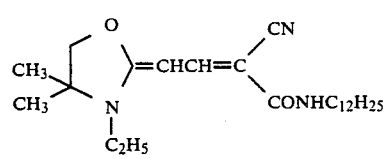

UV absorbent U-2

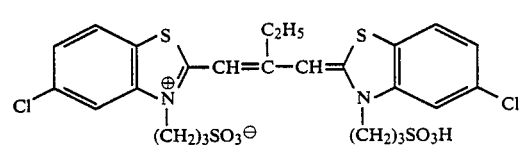

Sensitizing dye S-1

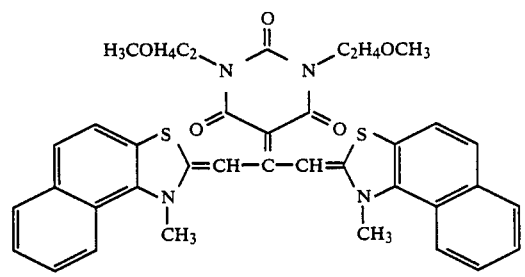

Sensitizing dye S-2

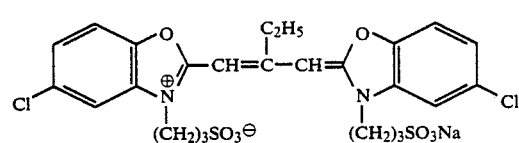

Sensitizing dye S-3

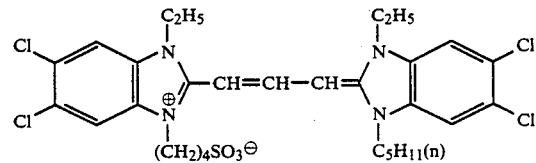

Sensitizing dye S-4

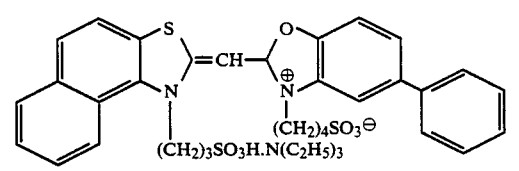

Sensitizing dye S-5

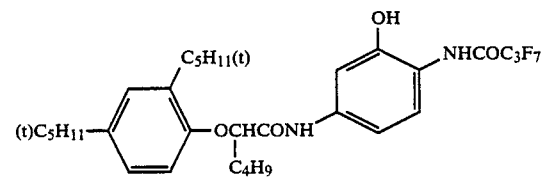

Coupler C-1

-continued

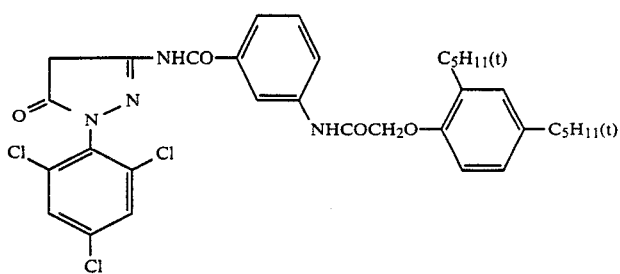

Coupler C-2

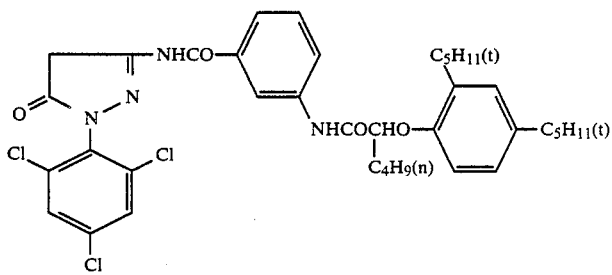

Coupler C-3

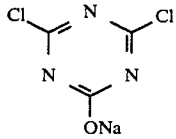

Gelatin hardener-1

$NaO_3SCHCOOCH_2(CF_2CF_2)_3H$
$\quad\quad |$
$\quad CH_2COOCH_2(CF_2CF_2)_3H$

Surfactant-1

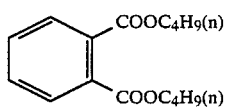

O-1

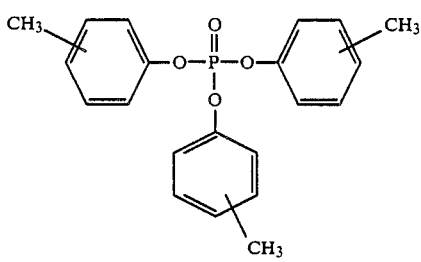

O-2

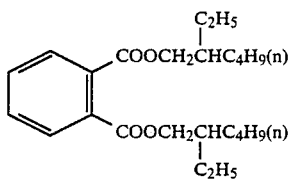

O-3

Further, Samples 41 through 49 were each prepared in the same manner as in Sample 40, except that the yellow couplers of Layers 10 and 11 of Sample 40 were changed to those shown in Table 5. The resulting samples were exposed wedgewise to light and processes in the following processing steps and with the following processing solutions.

| Processing step | Processing time | Processing temperature |
|---|---|---|
| First developing | 6 min. | 38° C. |
| Washing | 2 min. | 38° C. |
| Reversing | 2 min. | 28° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | At ordinary temperature |

| Processing step | Processing time | Processing temperature |
|---|---|---|
| Drying | | |

In the above processing steps, the processing solutions having the following compositions were used.

| First developer | |
|---|---|
| Sodium tetrapolyphosphate | 2 g |
| Sodium sulfite | 20 g |
| Hydroquinone.monosulfonate | 30 g |
| Sodium carbonate, monohydrate | 30 g |
| 1-phenyl-4-methyl-4-hydroxymethyl-3-pyrazolidone | 2 g |
| Potassium bromide | 2.5 g |
| Potassium thiocyanate | 1.2 g |
| Potassium iodide in a 0.1% solution | 2 ml |
| Add water to make | 1000 ml |
| Reversal solution | |
| Hexasodium nitrilotrimethylenesulfonate | 3 g |
| Stannous chloride, dihydrate | 1 g |
| P-Aminophenol | 0.1 g |
| Sodium hydroxide | 8 g |
| Glacical acetic acid | 15 ml |
| Add water to make | 1000 ml |
| Color developer | |
| Sodium tetrapolyphosphate | 3 g |
| Sodium sulfite | 7 g |
| Tertiary sodium phosphate, dihydrate | 36 g |
| Potassium bromide | 1 g |
| Potassium iodide in a 0.1% solution | 90 ml |
| Sodium hydroxide | 3 g |
| Citrazinic acid | 1.5 g |
| N-ethyl-N-β-methanesulfonamidoethyl-3-methyl-4-aminianiline. sulfate | 11 g |
| 2,2-ethylenedithiodiethanol | 1 g |
| Add water to make | 1000 ml |
| Moderater | |
| Sodium sulfite | 12 g |
| Sodium ethylenediaminetetraacetate, dihydrate | 8 g |
| Thioglycerol | 0.4 ml |
| Glacial acetic acid | 3 ml |
| Add water to make | 1000 ml |
| Bleacher | |
| Sodium ethylenediaminetetraacetate, dihydrate | 2 g |
| Ferric-ammonium ethylenediamine tetraacetate, duhydrate | 120 g |
| Ammonium bromide | 100 g |
| Add water to make | 1000 ml |
| Fixer | |
| Ammonium thiosulfate | 80 g |
| Sodium sulfite | 5 g |
| Sodium bisulfite | 5 g |
| Add water to make | 1000 ml |
| Stabilizer | |
| Formalin in a 37 wt % solution | 5 ml |
| Konidux, manufacture by KONICA CORP. | 5 ml |
| Add water to make | 1000 ml |

With the resulting samples, the densities thereof were measured through a blue filter. The results thereof are shown in Table 5, below.

TABLE 5

| Sample No. | Coupler No. | ΔFog*[1] | Maximum density |
|---|---|---|---|
| 40 Comparative | Y-1 | ±0 | 2.98 |
| 41 Comparative | Y-2 | +0.01 | 3.10 |
| 42 Comparative | Y-3 | +0.07 | 3.14 |
| 43 Comparative | Y-4 | +0.02 | 3.05 |
| 44 Invention | (2) | +0.01 | 3.34 |
| 45 Invention | (10) | +0.01 | 3.29 |
| 46 Invention | (14) | +0.03 | 3.27 |
| 47 Invention | (23) | +0.02 | 3.32 |

TABLE 5-continued

| Sample No. | Coupler No. | ΔFog*[1] | Maximum density |
|---|---|---|---|
| 48 Invention | (40) | +0.02 | 3.30 |
| 49 Invention | (55) | +0.03 | 3.36 |

*Difference in fog between each sample and Sample 40

As is obvious from Table 5 above, it was found that the yellow couplers of the invention can provide an excellent color density without increasing fog.

What is claimed is:

1. A silver halide color photographic light-sensitive material comprising a silver halide emulsion layer containing a coupler represented by the following Formula I:

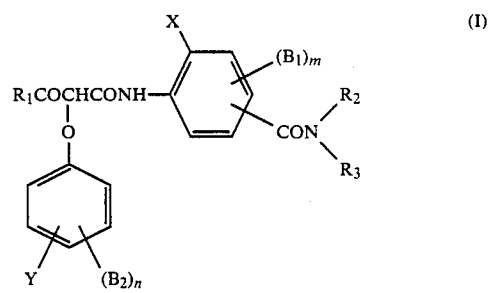

wherein $R_1$ is a substituted or unsubstituted aryl group; $R_2$ and $R_3$ are each a hydrogen atom, a substituted or unsubstituted alkyl group, a substituted or unsubstituted aryl group, or a substituted or unsubstituted heterocyclic group; X is a chlorine atom; Y, $B_1$ and $B_2$ are each a substituent, provided that Y or $B_2$ is bonded to the aryloxy group at the m- or p- position with respect to the oxygen atom; and m and n are each an integer of 0 to 3.

2. The material of claim 1, wherein said aryl group represented by said $R_1$ is an aryl group having 6 to 30 carbon atoms.

3. The material of claim 1, wherein said alkyl group represented by said $R_2$ and $R_3$ are each an alkyl group having 1 to 30 carbon atoms.

4. The material of claim 1, wherein said aryl group represented by said $R_2$ and $R_3$ are each an aryl group having 6 to 30 carbon atoms.

5. The material of claim 1, wherein said heterocyclic group represented by said $R_2$ and $R_3$ is a furyl group, a pyranyl group, a thienyl group, a pyridyl group or a 2H-pyrrolyl group.

6. The material of claim 1, wherein said substituent represented by Y is an electron attractive substituent.

7. The material of claim 6, wherein said electron attractive substituent is a halogen atom, an alkylcarbonylamino group, an aryl-carbonylamino group, an alkylsulfonylamino group, an aryl-sulfonylamino group, a nitro group, a cyano group, a carboxy group, an alkoxycarbonyl group, an aryloxycarbonyl group, a carbamoyl group, an alkylcarbamoyl group, an arylcarbamoyl group, an alkylcarbonyl group, an arylcarbonyl group, a sulfo group, an alkyl sulfonyl group, an arylsulfonyl group, a sulfamoyl group, an alkylsulfamoyl group or an arylsufamoyl group.

8. The material of claim 1, wherein said substituent represented by said $B_1$ is a halogen atom, an alkoxy group, an aryloxy group, an acyloxy group, an alkylamino group, an anilino group or an acylamino group.

9. The material of claim 1, wherein said substituent represented by $B_2$ is a halogen atom, an alkyl group, an alkenyl group, an aryl group, an alkoxy group, an aryloxy group, an acyloxy group, an alkylamino group, an anilino group, an alkylcarbonylamino group, an arylcarbonylamino group, an alkylsulfonylamino group, an aryl-sulfonylamino group, a nitro group, a cyano group, a carboxy group, an alkoxycarbonyl group, an aryloxycarbonyl group, a carbamoyl group, an alkylcarbamoyl group, an arylcarbamoyl group, an alkylcarbonyl group, an arylcarbonyl group, a mercapto group, a thioalkyl group, a thioaryl group, a sulfo group, an alkylsulfonyl group, an arylsulfonyl group, a sulfamoyl group, an alkylsulfamoyl group an arylsufamoyl group or a heterocyclic group.

* * * * *